US007638295B2

(12) United States Patent
Schofield et al.

(10) Patent No.: US 7,638,295 B2
(45) Date of Patent: Dec. 29, 2009

(54) ASSAYS FOR IDENTIFYING MODULATORS OF THE HYDROXYLATION OF ANKYRIN REPEAT PROTEINS BY 2-OXOGLUTARATE DEPENDENT OXYGENASE AND METHODS OF USING THE SAME

(75) Inventors: Christopher Joseph Schofield, Oxford (GB); Kirsty Sarah Hewitson, Oxford (GB); Michael Arnold McDonough, Oxford (GB); Peter John Ratcliffe, Oxford (GB); Norma Masson, Oxford (GB); Matthew Edward Cockman, Oxford (GB)

(73) Assignee: Isis Innovation Limited, Oxford (GB)

( * ) Notice: Subject to any disclaimer, the term of this patent is extended or adjusted under 35 U.S.C. 154(b) by 228 days.

(21) Appl. No.: 10/594,295

(22) PCT Filed: Mar. 24, 2005

(86) PCT No.: PCT/GB2005/001150

§ 371 (c)(1),
(2), (4) Date: Jan. 8, 2007

(87) PCT Pub. No.: WO2005/093411

PCT Pub. Date: Oct. 6, 2005

(65) Prior Publication Data

US 2008/0227848 A1    Sep. 18, 2008

(30) Foreign Application Priority Data

Mar. 26, 2004  (GB)  ................................. 0406914.2
Nov. 23, 2004  (GB)  ................................. 0425760.6

(51) Int. Cl.
*C12Q 1/26* (2006.01)
*C12N 9/02* (2006.01)
(52) U.S. Cl. ........................................ 435/25; 435/189
(58) Field of Classification Search ........................ None
See application file for complete search history.

(56) References Cited

U.S. PATENT DOCUMENTS

| 4,446,038 | A | 5/1984 | Schlicht et al. |
| 5,206,343 | A | 4/1993 | Henke et al. |
| 5,916,898 | A | 6/1999 | Edwards et al. |
| 6,200,974 | B1 | 3/2001 | Edwards et al. |
| 6,566,088 | B1 | 5/2003 | McKnight et al. |
| 2003/0153503 | A1 | 8/2003 | Klaus et al. |
| 2003/0176317 | A1 | 9/2003 | Guenzler-Pukall et al. |
| 2004/0053977 | A1 | 3/2004 | Almstead et al. |

FOREIGN PATENT DOCUMENTS

| WO | WO 02/074981 | 9/2002 |
| WO | 03/080566 | 10/2003 |
| WO | WO 03/100087 | 12/2003 |
| WO | WO 03/100438 | 12/2003 |
| WO | 2004/035812 | 4/2004 |

OTHER PUBLICATIONS

Wells, J.A. Additivity of Mutational Effects in Proteins; Biochemistry, vol. 29, No. 37 (1990) pp. 8509-8517.*
Seffernick et al. Melamine Deaminase and Atrazine Chlorohydrolase: 98 Percent identical but Functionally Different; Journal of Bacteriology, vol. 183, No. 8 (2001) pp. 2405-2410.*
Ciechanover et al., "Mechanisms of Ubiquitin-Mediated, Limited Processing of the NF-kappaB1 Precursor Protein p105," Biochimie 83:341-349, 2001.
Dann et al., "Structure of Factor-Inhibiting Hypoxia-Inducible Factor 1: an Asparaginyl Hydroxylase Involved in the Hypoxic Response Pathway," PNAS 99:15351-15356, 2002.
Elkins et al., "Structure of Factor-Inhibiting Hypoxia-Inducible Factor (HIF) Reveals Mechanism of Oxidative Modification of HIF-1alpha," J. Biol. Chem. 278:1802-1806, 2003.
Hewitson et al., "The Role of Iron and 2-Oxoglutarate Oxygenases in Signalling," Biochem. Soc. Trans. 31:510-515, 2003.
Lee et al., "Structure of Human FIH-1 Reveals a Unique Active Site Pocket and Interaction Sites for HIF-1 and von Hippel-Lindau," J. Biol. Chem. 278:7558-7563, 2003.
Mole et al., "2-Oxoglutarate Analogue Inhibitors of HIF Prolyl Hydroxylase," Bioorg. Med. Chem. Lett. 13:2677-2680, 2003.
Sedgwick et al., "The Ankyrin Repeat: a Diversity of Interactions on a Common Structural Framework," Trends Biochem. Sci. 24:311-316, 1999.
Asikainen et al., "Stabilization of HIF-1Alpha and Release of VEGF by Prolyl-4-Hydroxylase Inhibition in Human Lung Cells," Free Radical Bio. Med. 35:410 Suppl. 1, 2003.
Aoyagi et al., "Prolyl 4-Hydroxylase Inhibitor is More Effective for the Inhibition of Proliferation than for Inhibition of Collagen Synthesis of Rat Hepatic Stellate Cells," Hepatol. Res. 23:1-6, 2002.
Baader et al., "Inhibition of Prolyl 4-Hydroxylase by Oxalyl Amino Acid Derivatives in vitro, in Isolated Microsomes and in Embryonic Chicken Tissues," Biochem. J. 300:525-530, 1994.
Baader et al., "Interference in Clinical Laboratory Tests, with Special Regard to the Bilirubin Assay: Effects of a Metabolite of the New Prolyl 4-Hydroxylase Inhibitor, Lufironil," Eur. J. Clin. Chem. Clin. Biol. 32:515-520, 1994.
Bickel et al., "Beneficial Effects of Inhibitors of Prolyl 4-Hydroxylase in $CCl_4$-Induced Fibrosis of the Liver in Rats," J. Hepatol. 13(Suppl. 3):S26-S34, 1991.
Bickel et al., "Selective Inhibition of Hepatic Collagen Accumulation in Experimental Liver Fibrosis in Rats by a New Prolyl 4-Hydroxylase Inhibitor," Hepatol. 28:404-411, 1998.
Cunliffe et al., "Inhibition of Prolyl 4-Hydroxylase by Hydroxyanthraquinones," Biochem. J. 239:311-315, 1986.

(Continued)

*Primary Examiner*—Jon P Weber
*Assistant Examiner*—Paul C. Martin
(74) *Attorney, Agent, or Firm*—Clark & Elbing LLP

(57) ABSTRACT

A method of identifying an agent which modulates 2-oxoglutarate dependent oxygenase activity, the method comprising contacting a 2-oxoglutarate dependent oxygenase and a test agent in the presence of a substrate comprising one or more ankyrin repeat, or fragment thereof, in conditions under which the substrate is hydroxylated in the absence of the test agent; and determining hydroxylation of the substrate.

26 Claims, 8 Drawing Sheets

OTHER PUBLICATIONS

Cunliffe et al., "Novel Inhibitors of Prolyl 4-Hydroxylase 3.[1] Inhibition by the Substrate Analogue *N*-Oxaloglycine and Its Derivatives," J. Med. Chem. 35:2652-2658, 1992.

Dowell et al., "Novel Inhibitors of Prolyl 4-Hydroxylase, Part 4. Pyridine-2-Carboxylic Acid Analogues with Alternative 2-Substituents," Eur. J. Med. Chem. 28:513-516, 1993.

Franklin et al., "Inhibition of Collagen Hydroxylation by 2,7,8-Trihydroxyanthraquinone in Embryonic-Chick Tendon Cells," Biochem. J. 261:127-130, 1989.

Franklin et al., "Therapeutic Approaches to Organ Fibrosis," Int. J. Biochem. Cell Biol. 29:79-89, 1997.

Franklin et al., "Inhibition of Prolyl 4-Hydroxylase in vitro and in vivo by Members of a Novel Series of Phenanthrolinones," Biochem. J. 353:333-338, 2001.

Friedman et al., "Prolyl 4-Hydroxylase is Required for Viability and Morphogenesis in *Caenorhabditis elegans*," Proc. Natl. Acad. Sci. U.S.A. 97:4736-4741, 2000.

Hewitson et al., "Hypoxia-Inducible Factor (HIF) Asparagine Hydroxylase is Identical to Factor Inhibiting HIF (FIH) and is Related to the Cupin Structural Family," J. Biol. Chem. 277:26351-26355, 2002.

Higashide et al., "Alahopcin, a New Dipeptide Antibiotic Produced by *Streptomyces albulus* Subsp. *Ochragerus* Subsp. Nov.," J. Antibiot. 38:285-295, 1985.

Ivan et al., "Biochemical Purification and Pharmacological Inhibition of a Mammalian Prolyl Hydroxylase Acting on Hypoxia-Inducible Factor," Proc. Natl. Acad. Sci. U.S.A. 99:13459-13464, 2002.

Lerner et al., "X-Ray Crystal Structure of a Bisubstrate Inhibitor Bound to the Enzyme Catechol-*O*-Methyltransferase: A Dramatic Effect of Inhibitor Preorganization on Binding Affinity," Angew. Chem. Int. Ed. 40:4040-4042, 2001.

Mahon et al., "FIH-1: A Novel Protein that Interacts with HIF-1α and VHL to Mediate Repression of HIF-1 Transcriptional Activity," Genes Dev. 15:2675-2686, 2001.

Main et al., "The Folding and Design of Repeat Proteins: Reaching a Consensus," Curr. Opin. Struct. Biol. 13:482-489, 2003.

McNeill et al., "A Fluorescence-Based Assay for 2-Oxoglutarate-Dependent Oxygenases," Anal. Biochem. 336:125-131, 2005.

Mosavi et al., "The Ankyrin Repeat as Molecular Architecture for Protein Recognition," Protein Sci. 13:1435-1448, 2004.

Myilyharju et al., "Collagens and Collagen-Related Diseases," Ann. Med. 33:7-21, 2001.

Nwogu et al., "Inhibition of Collagen Synthesis with Prolyl 4-Hydroxylase Inhibitor Improves Left Ventricular Function and Alters the Pattern of Left Ventricular Dilatation after Myocardial Infarction," Circulation 104:2216-2221, 2001.

Ohta et al., "The Absolute Configuration of P-1894B, A Potent Prolyl Hydroxylase Inhibitor," Chem. and Pharm. Bulletin 32:4350-4359, 1984.

Philipp et al., "Prolyl 4-Hydroxylase Inhibition Induces HIF and Improved Cardiac Function after Myocardial Infarction," Circulation 106 (Suppl. S.):II-267, Abstract No. 1344, 2002 (Abstract only).

Schultz et al., "Smart, a Simple Modular Architecture Research Tool: Identification of Signaling Domains," Proc. Natl. Acad. Sci. U.S.A. 95:5857-5864, 1998.

Wang et al., "Structure of *Aquifex Aeolicus* KDO8P Synthase in Complex with R5P and PEP, and with a Bisubstrate Inhibitor: Role of Active Site Water in Catalysis," Biochem. 40:15676-15683, 2001.

Wu et al., "Mechanism-Based Inactivation of the Human Prolyl-4-Hydroxylase by 5-Oxaproline-Containing Peptides: Evidence for a Prolyl Radical Intermediate," J. Am. Chem. Soc. 121:587-588, 1999.

International Preliminary Report on Patentability from International Application No. PCT/GB2005/001150, Nov. 15, 2005.

* cited by examiner

SEQUENCE LISTING

<160> NUMBER OF SEQ ID NOS: 23

<210> SEQ ID NO 1
<211> LENGTH: 21
<212> TYPE: PRT
<213> ORGANISM: Homo sapiens

<400> SEQUENCE: 1

Tyr Leu Gly Ile Val Glu Leu Leu Val Ser Leu Gly Ala Asp Val Asn
1               5                   10                  15

Ala Gln Glu Pro Cys
            20

<210> SEQ ID NO 2
<211> LENGTH: 21
<212> TYPE: PRT
<213> ORGANISM: Homo sapiens

<400> SEQUENCE: 2

Ser Leu Pro Cys Leu Leu Leu Val Ala Ala Gly Ala Asp Val Asn
1               5                   10                  15

Ala Gln Glu Gln Lys
            20

<210> SEQ ID NO 3
<211> LENGTH: 21
<212> TYPE: PRT
<213> ORGANISM: Homo sapiens

<400> SEQUENCE: 3

Asn Ala Leu Val Thr Lys Leu Leu Leu Asp Cys Gly Ala Glu Val Asn
1               5                   10                  15

Ala Val Asp Asn Glu
            20

<210> SEQ ID NO 4
<211> LENGTH: 11
<212> TYPE: PRT
<213> ORGANISM: Homo sapiens

<400> SEQUENCE: 4

Val Ala Ala Gly Ala Asp Val Asn Ala Gln Glu
1               5                   10

<210> SEQ ID NO 5
<211> LENGTH: 4
<212> TYPE: PRT
<213> ORGANISM: Homo sapiens

<400> SEQUENCE: 5

Asp Val Asn Ala
1

<210> SEQ ID NO 6
<211> LENGTH: 31
<212> TYPE: DNA
<213> ORGANISM: Homo sapiens

<400> SEQUENCE: 6
gcctgccatg tttgaagctg ctggtggccg c                              31

```
<210> SEQ ID NO 7
<211> LENGTH: 31
<212> TYPE: DNA
<213> ORGANISM: Homo sapiens

<400> SEQUENCE: 7
gcggccacca gcagcttcaa acatggcagg c                               31

<210> SEQ ID NO 8
<211> LENGTH: 32
<212> TYPE: DNA
<213> ORGANISM: Homo sapiens

<400> SEQUENCE: 8
tctgggggta cagtcgcaga gctggtggag gc                              32

<210> SEQ ID NO 9
<211> LENGTH: 32
<212> TYPE: DNA
<213> ORGANISM: Homo sapiens

<400> SEQUENCE: 9
gcctccacca gcactgcgac tgtaccccca ga                              32

<210> SEQ ID NO 10
<211> LENGTH: 349
<212> TYPE: PRT
<213> ORGANISM: Homo sapiens

<400> SEQUENCE: 10
```

Met Ala Ala Thr Ala Ala Glu Ala Val Ala Ser Gly Ser Gly Glu Pro
1               5                   10                  15

Arg Glu Glu Ala Gly Ala Leu Gly Pro Ala Trp Asp Glu Ser Gln Leu
            20                  25                  30

Arg Ser Tyr Ser Phe Pro Thr Arg Pro Ile Pro Arg Leu Ser Gln Ser
        35                  40                  45

Asp Pro Arg Ala Glu Glu Leu Ile Glu Asn Glu Glu Pro Val Val Leu
    50                  55                  60

Thr Asp Thr Asn Leu Val Tyr Pro Ala Leu Lys Trp Asp Leu Glu Tyr
65                  70                  75                  80

Leu Gln Glu Asn Ile Gly Asn Gly Asp Phe Ser Val Tyr Ser Ala Ser
                85                  90                  95

Thr His Lys Phe Leu Tyr Tyr Asp Glu Lys Lys Met Ala Asn Phe Gln
            100                 105                 110

Asn Phe Lys Pro Arg Ser Asn Arg Glu Glu Met Lys Phe His Glu Phe
        115                 120                 125

Val Glu Lys Leu Gln Asp Ile Gln Gln Arg Gly Gly Glu Glu Arg Leu
    130                 135                 140

Tyr Leu Gln Gln Thr Leu Asn Asp Thr Val Gly Arg Lys Ile Val Met
145                 150                 155                 160

Asp Phe Leu Gly Phe Asn Trp Asn Trp Ile Asn Lys Gln Gln Gly Lys
                165                 170                 175

Arg Gly Trp Gly Gln Leu Thr Ser Asn Leu Leu Leu Ile Gly Met Glu
            180                 185                 190

Gly Asn Val Thr Pro Ala His Tyr Asp Glu Gln Gln Asn Phe Phe Ala
        195                 200                 205

Gln Ile Lys Gly Tyr Lys Arg Cys Ile Leu Phe Pro Pro Asp Gln Phe
    210                 215                 220

```
Glu Cys Leu Tyr Pro Tyr Pro Val His His Pro Cys Asp Arg Gln Ser
225                 230                 235                 240

Gln Val Asp Phe Asp Asn Pro Asp Tyr Glu Arg Phe Pro Asn Phe Gln
            245                 250                 255

Asn Val Val Gly Tyr Glu Thr Val Gly Pro Gly Asp Val Leu Tyr
        260                 265                 270

Ile Pro Met Tyr Trp His His Ile Glu Ser Leu Leu Asn Gly Gly
    275                 280                 285

Ile Thr Ile Thr Val Asn Phe Trp Tyr Lys Gly Ala Pro Thr Pro Lys
    290                 295                 300

Arg Ile Glu Tyr Pro Leu Lys Ala His Gln Lys Val Ala Ile Met Arg
305                 310                 315                 320

Asn Ile Glu Lys Met Leu Gly Glu Ala Leu Gly Asn Pro Gln Glu Val
            325                 330                 335

Gly Pro Leu Leu Asn Thr Met Ile Lys Gly Arg Tyr Asn
            340                 345

<210> SEQ ID NO 11
<211> LENGTH: 19
<212> TYPE: PRT
<213> ORGANISM: Homo sapiens

<400> SEQUENCE: 11

Asp Glu Ser Gly Leu Pro Gln Leu Thr Ser Tyr Asp Cys Glu Val Asn
1               5                   10                  15

Ala Pro Ile

<210> SEQ ID NO 12
<211> LENGTH: 20
<212> TYPE: PRT
<213> ORGANISM: Homo sapiens

<400> SEQUENCE: 12

Ser Leu Ser Met Val Gln Leu Leu Gln His Gly Ala Asn Val Asn
1               5                   10                  15

Ala Gln Met Tyr
        20

<210> SEQ ID NO 13
<211> LENGTH: 20
<212> TYPE: PRT
<213> ORGANISM: Homo sapiens

<400> SEQUENCE: 13

Phe Leu Asp Thr Leu Lys Val Leu Val Glu His Gly Ala Asp Val Asn
1               5                   10                  15

Val Pro Asp Gly
        20

<210> SEQ ID NO 14
<211> LENGTH: 20
<212> TYPE: PRT
<213> ORGANISM: Homo sapiens

<400> SEQUENCE: 14

His Ala Ser Ile Val Glu Val Leu Leu Lys His Gly Ala Asp Val Asn
1               5                   10                  15

Ala Lys Asp Met
        20
```

-continued

```
<210> SEQ ID NO 15
<211> LENGTH: 20
<212> TYPE: PRT
<213> ORGANISM: Homo sapiens

<400> SEQUENCE: 15

Asn Leu Glu Val Ala Glu Tyr Leu Leu Glu His Gly Ala Asp Val Asn
1               5                   10                  15

Ala Gln Asp Lys
            20

<210> SEQ ID NO 16
<211> LENGTH: 20
<212> TYPE: PRT
<213> ORGANISM: Homo sapiens

<400> SEQUENCE: 16

Val Glu Val Leu Lys Ile Leu Leu Asp Glu Met Gly Ala Asp Val Asn
1               5                   10                  15

Ala Cys Asp Asn
            20

<210> SEQ ID NO 17
<211> LENGTH: 20
<212> TYPE: PRT
<213> ORGANISM: Homo sapiens

<400> SEQUENCE: 17

Arg Asp Glu Ile Val Lys Ala Leu Leu Gly Lys Gly Ala Gln Val Asn
1               5                   10                  15

Ala Val Asn Gln
            20

<210> SEQ ID NO 18
<211> LENGTH: 20
<212> TYPE: PRT
<213> ORGANISM: Homo sapiens

<400> SEQUENCE: 18

Gln Leu Glu Ile Leu Glu Phe Leu Leu Leu Lys Gly Ala Asp Ile Asn
1               5                   10                  15

Ala Pro Asp Lys
            20

<210> SEQ ID NO 19
<211> LENGTH: 20
<212> TYPE: PRT
<213> ORGANISM: Homo sapiens

<400> SEQUENCE: 19

Tyr Thr Glu Val Leu Lys Leu Leu Ile Gln Ala Gly Tyr Asp Val Asn
1               5                   10                  15

Ile Lys Asp Tyr
            20

<210> SEQ ID NO 20
<211> LENGTH: 20
<212> TYPE: PRT
<213> ORGANISM: Homo sapiens
```

```
<400> SEQUENCE: 20

Asn Thr Arg Val Ala Ser Phe Leu Leu Gln His Asp Ala Asp Ile Asn
1               5                   10                  15

Ala Gln Thr Lys
            20

<210> SEQ ID NO 21
<211> LENGTH: 4
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = Asp, Glu, Asn or Gln
<220> FEATURE:
<221> NAME/KEY: MISC_FEATURE
<222> LOCATION: (2)..(2)
<223> OTHER INFORMATION: Xaa = Val, Ile or Leu
<220> FEATURE:
<221> NAME/KEY: MISC_FEATURE
<222> LOCATION: (4)..(4)
<223> OTHER INFORMATION: Xaa = Ala, Val or Ile

<400> SEQUENCE: 21

Xaa Xaa Asn Xaa
1

<210> SEQ ID NO 22
<211> LENGTH: 273
<212> TYPE: PRT
<213> ORGANISM: Homo sapiens

<400> SEQUENCE: 22

Thr Ala Val Gln Asp Glu Asn Gly Asp Ser Val Leu His Leu Ala Ile
1               5                   10                  15

Ile His Leu His Ser Gln Leu Val Arg Asp Leu Leu Glu Val Thr Ser
            20                  25                  30

Gly Leu Ile Ser Asp Asp Ile Ile Asn Met Arg Asn Asp Leu Tyr Gln
        35                  40                  45

Thr Pro Leu His Leu Ala Val Ile Thr Lys Gln Glu Asp Val Val Glu
    50                  55                  60

Asp Leu Leu Arg Ala Gly Ala Asp Leu Ser Leu Leu Asp Arg Leu Gly
65                  70                  75                  80

Asn Ser Val Leu His Leu Ala Ala Lys Glu Gly His Asp Lys Val Leu
                85                  90                  95

Ser Ile Leu Leu Lys His Lys Lys Ala Ala Leu Leu Leu Asp His Pro
            100                 105                 110

Asn Gly Asp Gly Leu Asn Ala Ile His Leu Ala Met Met Ser Asn Ser
        115                 120                 125

Leu Pro Cys Leu Leu Leu Leu Val Ala Ala Gly Ala Asp Val Asn Ala
    130                 135                 140

Gln Glu Gln Lys Ser Gly Arg Thr Ala Leu His Leu Ala Val Glu His
145                 150                 155                 160

Asp Asn Ile Ser Leu Ala Gly Cys Leu Leu Leu Glu Gly Asp Ala His
                165                 170                 175

Val Asp Ser Thr Thr Tyr Asp Gly Thr Thr Pro Leu His Ile Ala Ala
            180                 185                 190

Gly Arg Gly Ser Thr Arg Leu Ala Ala Leu Leu Lys Ala Ala Gly Ala
        195                 200                 205
```

```
-continued

Asp Pro Leu Val Glu Asn Phe Glu Pro Leu Tyr Asp Leu Asp Asp Ser
    210                 215                 220

Trp Glu Asn Ala Gly Glu Asp Glu Gly Val Val Pro Gly Thr Thr Pro
225                 230                 235                 240

Leu Asp Met Ala Thr Ser Trp Gln Val Phe Asp Ile Leu Asn Gly Lys
                245                 250                 255

Pro Tyr Glu Pro Glu Phe Thr Ser Asp Asp Leu Leu Ala Gln Gly Asp
            260                 265                 270

Met

<210> SEQ ID NO 23
<211> LENGTH: 7
<212> TYPE: PRT
<213> ORGANISM: Homo sapiens

<400> SEQUENCE: 23

Cys Gly Ala Asp Val Asn Arg
1               5
```

ASSAYS FOR IDENTIFYING MODULATORS OF THE HYDROXYLATION OF ANKYRIN REPEAT PROTEINS BY 2-OXOGLUTARATE DEPENDENT OXYGENASE AND METHODS OF USING THE SAME

CROSS-REFERENCE TO RELATED APPLICATIONS

This application claims priority under 35 U.S.C. §371 from international application PCT/GB2005/001150, filed Mar. 24, 2005, which claims priority from United Kingdom Patent Application 0406914.2, filed Mar. 26, 2004. International application PCT/GB2005/001150 also claims priority from United Kingdom Patent Application 0425760.6, filed Nov. 23, 2004.

FIELD OF THE INVENTION

The present invention relates to an assay for identifying modulators of the hydroxylation of ankyrin repeat proteins by 2-oxoglutarate dependent oxygenase. Agents which modulate such enzymatic activity are also provided.

BACKGROUND TO THE INVENTION

Reduced dioxygen concentration in the tissues of multicellular organisms triggers the hypoxic response that works to restore normoxia by improving the supply of oxygen to affected tissues. The response involves an array of genes including those encoding for erythropoietin and vascular endothelial growth factor and is mediated by an $\alpha\beta$-heterodimeric transcription factor, hypoxia-inducible factor (HIF), the $\alpha$-subunit of which is upregulated under hypoxic conditions. The genes involved in the hypoxic response include those involved in angiogenesis. Modulation of the hypoxic response is of interest from the perspectives of developing new therapies for both cancer, cardiovascular and other diseases.

The super-family of 2-OG and ferrous iron dependent enzymes catalyse a wide range of oxidative reactions including the hydroxylation of unactivated C—H bonds (such as in the conversion of proline to 4-hydroxyproline as catalysed by proline-4-hydroxylase), desaturation of C—C bonds and oxidative cyclisations.

In most cases enzymes belonging to the super-family of 2-OG oxygenases (as defined by their structural relationship, requirement for dioxygen as cosubstrate, and a requirement for ferrous iron as a cofactor) actually use 2-OG as a cosubstrate. In these cases the 4-electron oxidising power of a dioxygen molecule is coupled to the two-electron oxidation of the substrate (e.g. proline to 4-hydroxyproline in reactions catalysed by proline-4-hydroxylase) and the oxidation of 2-OG to give succinate and $CO_2$ (Que Nat. Struct. Biol. (2000) 7 182-184).

The stoichiometry of a typical hydroxylation reaction as catalysed by a 2-OG oxygenase, such as FIH or a PHD enzyme, is as follows:

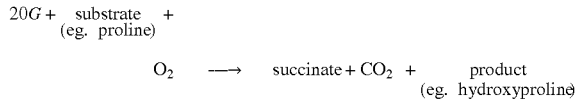

Certain 2-OG oxygenases, including the prolyl hydroxylase domain (PHD also known as EGLN and HPH) enzymes, PHD1, PHD2, PHD3, and factor inhibiting hypoxia-inducible factor (FIH), are current targets for medicinal chemistry. Inhibition of the PHDs, and of FIH, is recognised as a means of inducing the hypoxic response for use in a therapeutic manner.

The sequence of FIH and its crystal structure coupled to bioinformatic analyses has identified FIH (i) as a 2-OG oxygenase that contains a double stranded beta-helix or jelly roll structural element, (ii) that FIH is a member of the so called JmjC family of proteins. The JmjC proteins are related to the cupin family as each contain, or are predicted to contain, at least one jelly roll structural element. Some of the JmjC proteins have been identified as being involved in important biological processes or disease states, e.g. congenital heart disease. It has been proposed that many of the JmjC proteins are 2-OG oxygenases involved in transcriptional regulation. A problem in the field is defining the substrates for the 2-OG oxygenases, some of which are characterised as JmjC proteins, which are involved in transcriptional regulation and other signalling pathways.

Currently there are over 400 JmjC domain proteins in the SMART domain database (Shultz et al. PNAS (1998) 95 5857-5864). A number of these are recognised as being gene products that are involved in regulation of chromatin structure and hence transcriptional control (Clissold and Ponting TIBS (2001) 26 7-9).

The ankyrin (ANK) repeat motif is composed of two antiparallel $\alpha$-helices followed by a beta-bulge and beta-hairpin containing loop connecting it to the next repeat, each of which contain 33 residues (FIG. 1). The repeats occur in tandem from several up to 24 repeats (for review see Sedgwick and Smerdon TIBS (1999) 24 311-316). The extended beta-hairpin containing loops, or "fingers", form a groove on the surface.

Currently, over 3500 sequences containing ANK can be found listed in the SMART domain database (Shultz et al. PNAS (1998) 95 5857-5864). Of these 3500 sequences, over 3000 are from eukaryotes, 135 from bacteria, and 4 from archaea. Of the 3000 eukaryotic ANK-protein sequences, over 2600 are from metazoans and over 600 each from human and mouse. Many ankyrin proteins are also present in plants where they are involved in regulation and signaling.

Proteins containing ANK repeats are often involved in protein-protein interactions. The highly conserved core serves as a scaffold for the variable surface exposed residues especially in the "fingers", which are involved in most interactions with other proteins (Sedgwick and Smerdon TIBS (1999) 24 311-316). Their functions vary widely and include cyclin-dependent kinase (CDK) inhibitors, transcriptional regulators, cytoskeletal organizers, developmental regulators and even toxins. Defects in ankyrin repeat proteins have been found in a number of human diseases.

SUMMARY OF THE INVENTION

The present inventors have identified a number of previously unknown substrates for FIH. These substrates all contain the ankyrin structural element, or a fragment thereof. The inventors have thus established a link between the JmjC proteins and the ankyrin proteins and have identified a novel mechanism of transcriptional regulation in which ankyrin proteins are hydroxylated by JmjC proteins. The ankyrin proteins shown to be substrates for FIH are involved in various biological pathways that are important from a therapeutic perspective, including signalling pathways associated with ischaemic disease, cancer, inflammation and immunity.

2-OG oxygenases and ankyrin substrates, or fragments thereof, may thus be used in assays/screens for identifying modulators, such as inhibitors and activators, of 2-OG oxygenases, such as FIH and other members of the JmjC family of 2-OG oxygenases. Inhibitors and activators are agents that inhibit or enhance hydroxylation of ankyrin substrates, or fragments thereof, by 2-OG oxygenases.

In addition, such assays/screens may be used to identify modulators which are selective for 2-OG oxygenases that hydroxylate ankyrins or for 2-OG oxygenases that do not act on ankyrins. Such assays/screens may also be used to identify modulators that are selective for activity of a single 2-OG oxygenase on a particular substrate or group of substrates.

Modulators identified by such assays/screens are useful in medicine, for example in the treatment of ischaemic disease, cancer, inflammation, immunity, anaemia and beta thalassemia.

Accordingly, the present invention provides:

a method of identifying an agent which modulates 2-oxoglutarate dependent oxygenase activity, the method comprising:
(i) contacting a 2-oxoglutarate dependent oxygenase and a test agent in the presence of a substrate comprising one or more ankyrin repeat, or fragment thereof, in conditions under which the substrate is hydroxylated in the absence of the test agent; and
(ii) determining hydroxylation of the substrate;
thereby determining whether or not the agent modulates 2-oxoglutarate dependent oxygenase activity;

a method of identifying an agent which selectively modulates activity of a first 2-oxoglutarate dependent oxygenase, the method comprising:
(a)(i) contacting a first 2-oxoglutarate dependent oxygenase and a test agent in the presence of a substrate comprising one or more ankyrin repeat, or fragment thereof, in conditions under which the substrate is hydroxylated in the absence of the test agent; and
(ii) determining hydroxylation of the substrate;
(b)(i) contacting a second 2-oxoglutarate dependent oxygenase and a test agent in the presence of a substrate comprising one or more ankyrin repeat, or fragment thereof, in conditions under which the substrate is hydroxylated in the absence of the test agent; and
(ii) determining hydroxylation of the substrate;
thereby determining whether or not the agent selectively modulates activity of the first 2-oxoglutarate dependent oxygenase; and a method of identifying an agent which selectively modulates 2-oxoglutarate dependent oxygenase activity on a first substrate, the method comprising:
(a)(i) contacting a 2-oxoglutarate dependent oxygenase and a test agent in the presence of a first substrate, or fragment thereof, in conditions under which the substrate is hydroxylated in the absence of the test agent; and
(ii) determining hydroxylation of the first substrate; and
(b)(i) contacting a 2-oxoglutarate dependent oxygenase and a test agent in the presence of a second substrate, or fragment thereof, in conditions under which the substrate is hydroxylated in the absence of the test agent; and
(ii) determining hydroxylation of the second substrate;
wherein at least one of said first and second substrates comprises one or more ankyrin repeat,
thereby determining whether or not the agent selectively modulates 2-oxoglutarate dependent oxygenase activity on a first substrate.

The substrate is preferably hydroxylated at an asparagine residue. The asparagine residue is part of a valine-asparagine, aspartate-valine-asparagine or isoleucine-asparagine sequence. Preferred substrates include IκB-α, p105, FEM-1, p19-NK-4d, GABPbeta, Tankyrase ½, 2-5A-d-R, Gankyrin, Myotrophin, M110, FGIF (factor inducing foetal globin), and fragments, derivatives and analogues thereof. The 2-oxoglutarate dependent oxygenase is preferably a JmjC protein. The JmjC protein is preferably factor inhibiting hypoxia-inducible factor (FIH).

A method of the invention may further comprise formulating an agent identified as a modulator of 2-oxoglutarate dependent oxygenase activity with a pharmaceutically acceptable recipient.

An agent identified by an assay method according to the invention is also provided. An agent of the invention is provided for use in a method of treatment of the human or animal body by therapy. The invention also provides the use of a agent of the invention in the manufacture of a medicament for the treatment of a condition associated with increased or decreased levels or activity of an ankyrin repeat-containing protein or the treatment of a condition where it is desired to modulate activity of an ankyrin repeat-containing protein. The invention also provides a method of treating a condition associated with increased or decreased levels or activity of an ankyrin repeat-containing protein or the treatment of a condition where it is desired to modulate activity of an ankyrin repeat-containing protein, comprising administering a therapeutically effective amount of an agent according to the invention to an individual in need thereof. The condition is preferably selected from the group consisting of ischemia, cancer, inflammatory disorders, immune disorders, anaemia and thalassemia.

The invention additionally provides a method of modulating ankyrin repeat-containing protein mediated activity in a cell in vivo or in vitro comprising contacting the cell with an agent which inhibits the asparagine hydroxylase activity of a 2-oxoglutarate dependent oxygenase.

The invention also provides the use of a polypeptide comprising an ankyrin repeat or analogue thereof, or a polynucleotide encoding said polypeptide, in an in vitro or in vivo method of inhibiting a 2-oxoglutarate oxygenase and a polypeptide comprising a ankyrin repeat sequence analogue which is not susceptible to hydroxylation by a 2-oxoglutarate oxygenase for use in a method of treatment of the human or animal body.

BRIEF DESCRIPTION OF THE SEQUENCES

Figure 1:
FIG. 1 is a ribbon representation of the structure of ANK-repeat protein IκB-α-NFκB complex with NFκB removed (1nfi). Repeats are numbered N-terminal to C-terminal from 1-6.

SEQ ID NO: 1 is a fragment of IκB-α that is hydroxylated at the asparagine residue by FIH.

SEQ ID NO: 2 is a fragment of p105 that is hydroxylated at the asparagine residue by FIH.

SEQ ID NO: 3 is a fragment of FEM-1 that is hydroxylated at the asparagine residue by FIH.

SEQ ID NO: 4 is a fragment of p105 that is hydroxylated at the asparagine residue by FIH.

SEQ ID NO: 5 is the conserved consensus sequence hydroxylated at the asparagine residue by FIH.

SEQ ID NO: 6 to SEQ ID NO: 9 are the nucleic acid sequences of primers used in the Examples.

SEQ ID NO: 10 is the amino acid sequence of FIH.

SEQ ID NO: 11 is the amino acid sequence of CAD, which is a HIF C-terminal transactivation domain standard peptide.

SEQ ID NO: 12 is a fragment of Bcl-3 that is hydroxylated by FIH.

SEQ ID NO: 13 is a fragment of P19-INK4d that is hydroxylated by FIH.

SEQ ID NO: 14 is a fragment of GABPbeta that is hydroxylated by FIH.

SEQ ID NO: 15 is a fragment of Tankyrase that is hydroxylated by FIH.

SEQ ID NO: 16 is a fragment of 2-5A-d-R that is hydroxylated by FIH.

SEQ ID NO: 17 is a fragment of Gankyrin/p28-II that is hydroxylated by FIH.

SEQ ID NO: 18 is a fragment of Myotrophin that is hydroxylated by FIH.

SEQ ID NO: 19 is a fragment of M110 that is hydroxylated by FIH.

SEQ ID NO: 20 is a fragment of FGIF that is hydroxylated by FIH.

SEQ ID NO: 22 is a sequence motif comprising the asparagine residue hydroxylased by 2-OG oxygenases.

SEQ ID NO: 22 is the amino acid sequence of the p105 ankyrin repeat domain (ARD).

SEQ ID NO: 23 is the amino acid sequence of a peptide fragment of IKB-α that is hydroxylated endogenously.

DETAILED DESCRIPTION OF THE INVENTION

Assay

The present inventors have shown that hydroxylation of proteins containing an ankyrin repeat or a fragment of an ankyrin repeat comprising an asparagine residue is mediated by 2-oxoglutarate (2-OG) dependent oxygenases. The action of 2-OG dependent oxygenases, and in particular human 2-OG dependent oxygenases, represent a novel target for the control of ankyrin repeat containing proteins.

In particular, the inventors have shown that IκB-α is hydroxylated by FIH. IκB-α plays a role in sequestering the NFκB heterodimers, which are composed of p50 and p65 subunits, in the cytoplasm. An N-terminal signal recognition domain on IκB-α is a target of phosphorylation that mediates IκB-α degradation. When IκB-α is degraded and its cellular concentration levels are low, free NFκB is translocated to the nucleus where it associates with various activators and initiates the transcription of many genes involved in the inflammatory response.

Since the NFκB pathway is known to be important in the inflammatory response, modulation of the activity of the ankyrin proteins in the pathway, e.g. by inhibition of 2OG oxygenases that modify ankyrin proteins, so that their stability is altered is useful for treatments of diseases associated with the inflammatory response. Desirable medicinal effects include the regulation of inflammation and immunity such as is achieved by reducing or increasing the interaction between NFκB proteins such as p105 and IκB-α and the p50/p65 transcriptional complex.

Ankyrin proteins are also associated with other disease states including cancer and apoptosis. Modulation of the biological properties, such as concentration and stability, of ankyrin proteins is thus useful for the inhibition of survival of tumour cells such as might be achieved by promoting interaction of p53 and ASPP1 or 2 or decreasing interaction of p53 with iASPP, or other means, and such as might act against cancerous tissues.

Similarly, proliferation and/or inhibition of apoptosis such as might be achieved by reducing interaction of the tumour suppressor proteins p16 or p18 with cyclin dependent kinases or other means, for example to improve ischaemic or hypoxia or otherwise damaged tissues.

A number of different assays are described below which may be carried out to identify modulators of 2-oxoglutarate dependent oxygenase activity using a protein containing one or more ankyrin domain(s) or fragment thereof as a substrate.

Typically, the assays utilise a human 2-OG dependent oxygenase such as FIH or a fragment or variant of a human 2-OG dependent oxygenase. A non-human 2-OG dependent oxygenase, or a fragment or variant thereof, may also be used. These components are described in more detail below. Each of these components, where required may be provided either in purified or unpurified form, for example, as cellular extracts or by purification of the relevant component from such extracts. Alternatively, the relevant component can be expressed using recombinant expression techniques and purified for use in the assay. Alternatively, the components may be expressed recombinantly in a cell for use in cell based assays.

Assay conditions can be optimised using standard techniques which involve screening of commercially available reagents or reagents described in the art.

Typically, a polynucleotide encoding the relevant component is provided within an expression vector. Such expression vectors are routinely constructed in the art and may for example involve the use of plasmid DNA and appropriate initiators, promoters, enhancers and other elements, such as for example polyadenylation signals which may be necessary and which are positioned in the correct orientation in order to allow full protein expression. Suitable vectors would be very readily apparent to those of skill in the art. Promoter sequences may be inducible or constitutive promoters depending on the selected assay format. The promoter may be tissue specific.

Assay Methods

The present invention provides an assay method for identifying an agent which modulates 2-OG dependent oxygenase activity on a substrate containing an ankyrin repeat or fragment thereof and, in particular for monitoring asparagine hydroxylation of an asparagine residue in the ankyrin repeat or fragment thereof. The method comprises contacting a 2-OG dependent oxygenase and a test substance, such as a potential inhibitor or activator, in the presence of a substrate of the 2-OG dependent oxygenase under conditions in which asparagine hydroxylation occurs in the absence of the test substance and determining the extent of asparagine hydroxylation of the substrate. Alternatively, the assay may be used to detect substances that increase the activity of the 2-OG dependent oxygenase by assaying for increases in activity.

In the experiments described herein, FIH has been found to hydroxylate IκB-α, p105, FEM-1, p19-INK-4d, GABPbeta, Tankyrase ½, 2-5A-d-R, Gankyrin, Myotrophin, M110, FGIF and peptide fragments thereof comprising an asparagine residue. IκB-α and p105 in particular are involved in signalling pathways controlling transcriptional activation and so modulating the hydroxylation of these proteins modulates transcriptional activation. This inhibition or activation of transcriptional activation may also be used as the basis for an assay of the invention.

Such assays of the present invention may be used to identify inhibitors of 2-OG dependent oxygenase activity and are thus preferably carried out under conditions under which asparagine hydroxylation would take place in the absence of the test substance. In the alternative, the assays may be used to look for promoters of asparagine hydroxylase activity, for example, by looking for increased hydroxylation of asparagine substrates compared to assays carried out in the absence of a test substance. The assays may also be carried out under conditions in which hydroxylation is reduced or absent, such as under hypoxic conditions and the presence of or increased hydroxylation could be monitored under such conditions. The assays of the invention may also be used to identify inhibitors or activators which are specific for 2-OG dependent oxygenases which have asparagine hydroxylase activity on an ankyrin-repeat containing protein and which do not have activity or are less active with other hydroxylases, for example, such as prolyl hydroxylases.

The present invention also provides an assay method for the identification of 2-OG dependent oxygenases that have asparagine hydroxylase activity on ankyrin repeat containing proteins. The method typically comprises providing a test polypeptide; bringing into contact an ankyrin repeat-containing protein and the test polypeptide under conditions in which the ankyrin repeat containing protein is hydroxylated at an asparagine residue by FIH, or other 2-OG oxygenase, and determining whether or not the ankyrin repeat-containing protein is hydroxylated at the asparagine residue.

2-oxoglutatarate Dependent Oxygenase

The 2-OG oxygenase used in an assay of the invention may be any member of the super-family of 2-OG and ferrous iron dependent enzymes which catalyses hydroxylation of one or more ANK-protein(s). The terms 2-OG oxygenase and 2-OG dependent oxygenase are used interchangeably herein.

Typically, the 2-OG oxygenase is a member of the JmjC family or cupin family of proteins (Hewitson et al., 2002, J. Biol. Chem. 277:26351-26355). The 2-OG dependent oxygenase preferably contains the structural element known as a double stranded beta-helix or jelly roll motif. Preferably the JmjC protein is involved in regulation of chromatin structure and hence transcriptional control. More preferably the JmjC protein is FIH.

Other 2-OG dependent oxygenases that may be used in an assay of the invention include, for example, clavaminte synthase, deacetoxycephalosporin C synthase, collagen-prolyl-4-hydroxylase, collagen prolyl-3-hydroxylase, lysyl hydroxylase, aspartyl hydroxylase, phytanoyl coenzyme A hydroxylase or gamma-butyrobetaine hydroxylase. 2OG dependent oxygenases may be mammalian, preferably human polypeptides.

Human 2-OG oxygenases include AlkB, collagen prolyl hydroxylases, lysine hydroxylases, the aspartyl/asparagine hydroxylase known to hydroxylate endothelial growth factor domains, phytanoyl CoA hydroxylase, gamma-butyrobetaine hydroxylase, trimethyl lysine hydroxylase, HIF prolyl hydroxylase isoforms including PHD1, PHD2, PHD3, and enzymes closely related to FIH. Enzymes closely related to FIH may include those proteins in the SWALL database that are referenced by the following numbers: Q9NWJ5, Q8TB10, Q9Y4E2, O95712, Q9H8B1, Q9NWT6 in *Homo sapiens*, and Q91W88 and Q9ER15 in *Mus musculus* and homologues of these enzymes.

The amino acid sequence of FIH is shown in SEQ ID NO: 10. The FIH used in a method of the invention may comprise the sequence shown in SEQ ID NO: 10 or may be a fragment or variant thereof.

In some embodiments, it is desirable to use a variant (mutant) form of a 2-OG oxygenase in an assay of the invention. For example, the variant may have increased solubility compared to the naturally occurring enzyme.

A variant or fragment of FIH for use in an assay of the invention has the ability to hydroxylate one or more residues of an ankyrin repeat-containing protein, preferably at an asparaginyl residue and in particular Asn 778 of p105. Preferably, a variant of FIH has at least 60% sequence identity with the amino acid sequence of SEQ ID NO: 2, preferably greater than 70%, more preferably greater than about 80%, 90%, 95% or 99% sequence identity. Such variants may include allelic variants and the deletion, modification or addition of single amino acids or groups of amino acids within or at one or both ends of the protein sequence, as long as the peptide retains asparagine hydroxylase activity. Preferably a variant of SEQ ID NO: 10 will have the same domain structure as FIH, i.e. an eight strand β barrel jelly roll.

Amino acid substitutions may be made, for example from 1, 2 or 3 to 10, 20 or 30 substitutions. Conservative substitutions may be made, for example according to the following Table. Amino acids in the same block in the second column and preferably in the same line in the third column may be substituted for each other.

| ALIPHATIC | Non-polar | G A P |
| --- | --- | --- |
| | | I L V |
| | Polar-uncharged | C S T M |
| | | N Q |
| | Polar-charged | D E |
| | | K R |
| AROMATIC | | H F W Y |

Variant polypeptides within the scope of the invention may be generated by any suitable method, for example by gene shuffling (molecular breeding) techniques.

A functional mimetic or derivative of FIH may also be used in an assay of the invention which has hydroxylase activity and in particular maintains ankyrin repeat asparagine hydroxylase activity. Such an active fragment may be included as part of a fusion protein, e.g. including a binding portion for a different i.e. heterologous ligand.

The oxygenase and substrate protein for use in an assay of the invention may be chemically modified, e.g. post-translationally modified. For example, the 2-OG oxygenase may have undergone proteolysis or may be glycosylated, hydroxylated, phosphorylated, acetylated, methylated or comprise modified amino acid residues. They may also be modified by the addition of histidine residues to assist their purification or by the addition of a nuclear localisation sequence to promote translocation to the nucleus or by post translational modification including hydroxylation or phosphorylation.

Substrate

The substrate used in an assay of the invention comprises one or more ankyrin repeat(s), or one or more fragment(s) of the ankyrin repeat. The substrate comprises at least one ankyrin repeat or fragment thereof which comprises an asparagine residue which is hydroxylated by the 2-OG dependent oxygenase.

An ankyrin repeat amino acid sequence is capable of folding forming a structural ankyrin repeat motif. The ankyrin repeat motif is composed of two anti-parallel α-helices followed by a beta-bulge and beta-hairpin containing loop connecting it to the next repeat, each of which contain 33 residues (FIG. 1). The substrate may comprise one such repeat or two or more, for example from 3 to 24, 5 to 20 or 8 to 12 repeats. The extended beta-hairpin containing loops, or "fingers", form a groove on the surface.

The substrate may be in a folded or unfolded form. Thus, the substrate may comprise all or part of a polypeptide sequence capable of folding to form two anti-parallel α helicies, a β-bulge and β-hairpin loop but in an unfolded, or partially folded form. Typically, where the substrate comprises three or more ankyrin repeat sequences, the substrate is in folded form.

The substrate may comprise one or more fragment of an ankyrin repeat which fragment is capable of being hydroxylated. The fragment preferably comprises an asparagine residue. The fragment is typically at least 5 amino acids in length, preferably at least 10, at least 15, at least 20 or at least 30 amino acids in length. The fragment typically encompasses the sequence which, in the ankyrin repeat containing protein folds to form beta-bulge before the beta-hairpin turn. Preferably, the fragment includes the sequence motif DVNA. Other preferred motifs are VN, DVN, LN and IN. The sequence motif may be of the formula:

wherein:
AA$_1$ is D, E, N or Q (preferably D)
AA$_2$ is V, L or I (preferably V)
AA$_3$ is A, V or I (preferably A).

The fragment preferably comprises at least one amino acid, for example at least 2, 3, 4, 5, 8 or 10 amino acids, on either one or both sides of the said sequence motif. The additional amino acids are preferably N-terminal to the said sequence motif.

Fragments of HIF comprising the DVNA motif are not included among the substrate useful in a method of the invention. In HIF, the DVNA motif does not form part of an ankyrin repeat.

Currently, over 3500 sequences containing ANK can be found listed in the SMART domain database (Shultz et al. PNAS (1998) 95 5857-5864). Of these 3500 sequences, over 3000 are from eukaryotes, 135 from bacteria, and 4 from archaea. Of the 3000 eukaryotic ANK-protein sequences, over 2600 are from metazoans and over 600 each from human and mouse. Many ankyrin proteins are also present in plants where they are involved in regulation and signaling. Preferably, the substrate is a human ANK-protein, or a fragment or derivative of such a human protein.

The substrate is typically a protein involved in protein-protein interactions, or a fragment or derivative of such a protein. The substrate may comprise the highly conserved core of an ANK-protein involved in protein-protein interactions, which core serves as a scaffold for the variable surface exposed residues especially in the "fingers", which are involved in most interactions with other proteins (Sedgwick and Smerdon TIBS (1999) 24 311-316).

The ANK-protein may be a cyclin-dependent kinase (CDK) inhibitor such as p19-INK-4d; transcriptional regulator such as GABPbeta; cytoskeletal organizer; developmental regulator such as Myotropin; toxin; enzyme such as the poly (ADP-ribose) polymerase, Tankyrase ½ or the endoribonuclease 2-5A(adenine)-dependent RNase (RNase L); or other regulator protein such as Gankyrin which is a regulator of retinoblastoma (Rb) protein, M110 (MYPTI) which is a regulator of myosin phosphorylation or factor inducing foetal globin (FGIF) which regulates foetal hemoglobin (Hb) expression. The substrate may be a fragment, derivative or analogue of any one of these proteins provided that it comprises an ankyrin repeat.

The substrate may be a naturally occurring protein or a recombinant or synthetic protein. For example, the synthetic protein may comprise one or more idealized ankyrin repeat such as those described in Main et al. Current Opin. Struct. Biol. 13:482-489 (2003).

In one preferred embodiment, the ANK-protein is involved in an NFκB signalling pathway. The substrate may be IκB-α Myotrophin which binds NKκB, or a fragment, derivative or analogue thereof. The substrate may be IκB-α or a fragment, derivative or analogue thereof. Preferred fragments of IκB-α include all or part of the sequence shown in SEQ ID NO: 1 and encompass the N residue at position 16 of SEQ ID NO: 1.

IκB is hydroxylated by FIH. Thus, in a preferred assay the 2-OG oxygenase is FIH and the substrate is IκB-α or a fragment, derivative or analogue thereof.

The substrate may be the NFκB protein p105 or a fragment, derivative or analogue thereof. Preferred fragments of p105 include all or part of the sequence shown in SEQ ID NO: 2 or 4 and encompass the N residue at position 16 of SEQ ID NO: 2. Examples of derivatives of p105 are given in the Examples. Preferred fragments of p105 thus comprise Asn 778 of p105 and preferred peptide analogues of p105, and fragments thereof, comprise an asparagine equivalent to Asn 778 of p105. A longer preferred fragment of p105 is the p105 ankyrin repeat domain (ARD) that encompasses amino acids 537 to 809 of p105 and is shown in SEQ ID NO: 22.

A further preferred substrate is FEM-1 or a fragment, derivative or analogue thereof. Preferred fragments of FEM-1 include all or part of the sequence shown in SEQ ID NO: 3 and encompass the N residue at position 16 of SEQ ID NO: 3.

NOTCH is another preferred ankyrin protein for use as a substrate. Fragments, derivatives or analogues of NOTCH may also be used in an assay of the invention.

Derivatives or analogues of the ankyrin repeat containing proteins, and fragments thereof, mentioned herein include proteins from other species having the same function as any one of the defined ankyrin repeat containing proteins and which share some sequence identity the said defined protein, and fragments thereof. Preferably, such analogues or derivatives have at least 60%, at least 70%, at least 80%, preferably at least 90%, at least 95% or at least 98% identity to the said protein or fragment. Derivatives and fragments therefore also include proteins and fragments in which one or more amino acid deletion, substitution or insertion has been made. The modification(s), deletion(s) or insertion(s) may be of a single amino acid or a group of amino acids, for example from 2 or 3 to 10 or 12 substitutions, within the protein sequences, as long as the protein retains on asparagine residue which may be hydroxylated by a 2-OG oxygenase. Conservative substitutions may be made according to the Table above.

In an assay where hydroxylation is determined by monitoring the interaction of the ANK-protein with another signally molecule, the assay is typically carried out under conditions suitable for that interaction to occur. Where the substrate is a fragment of an ANK-protein the fragment is one which comprises a domain that interacts with the other signaling molecule in addition to the asparagine residue for hydroxylation.

The agent may increase or decrease the interactions of the ankyrin protein and its cognate binding partner. For example, for Myotrophin, IκB-α, NOTCH or p105 the binding partner may be but is not limited to the tumour suppressor gene product p53, the NF-κB transcription factors p50/p65, the transcriptional complex CSL/Mastermind or the Ets protein GABP. For GABPbeta, the binding partner is typically GABPalpha. The binding partner for Tankyrase ½ may be any one of its multiple substrates such as TRF1, IRAP and Grb 14. The binding partner of Gankyrin may be CD4K/cyclin D or Rb and the binding partner of M110 may be protein phosphatase Ic.

Methods for Monitoring Modulation

The precise format of any of the screening or assay methods of the present invention may be varied by those of skill in the art using routine skill and knowledge. The skilled person is well aware of the need to additionally employ appropriate controlled experiments. The assays of the present invention may involve monitoring for asparagine hydroxylation of a substrate comprising one or more ankyrin domain(s) or fragment thereof, monitoring for the utilisation of substrates and co-substrates (for example, the consumption (i.e. depletion) of 2-OG, oxygen or substrate), or monitoring for the production of the expected products between the enzyme and its substrate. For example, the production of succinate or carbon dioxide, for example from radiolabelled 2-OG may be monitored. Activity may also be measured by derivatisation of 2-OG with ortho-phenylenediamine or other aromatic diamines, such as either 1,2-dimethoxy-4,5-diaminobenzene, or 1,2-methylenedioxy-4,5-diaminobenzene, such that the derivative gives improved sensitivity compared to ortho-phenylenediamine.

Assay methods of the present invention may also involve screening for the direct interaction between components in the system. Alternatively, assays may be carried out which monitor for downstream effects such as binding of the ankyrin repeat containing substrate to other proteins in a signalling pathway and downstream effects mediated by the ankyrin repeat containing protein such as transcriptional activation. Transcriptional activation may be monitored using suitable reporter constructs or by monitoring for the upregulation of genes or alterations in the expression patterns of genes known to be regulated directly or indirectly by the ankyrin repeat containing protein.

Various methods for determining hydroxylation are known in the art and are described and exemplified herein. Any suitable method may be used for determining activity of the 2-OG dependent oxygenase such as by substrate or co-substrate utilization, product appearance such as peptide hydroxylation or down-stream effects mediated by hydroxylated or non-hydroxylated products.

The identification of ankyrin-repeat containing proteins as a substrate for 2-OG dependent oxygenases such as FIH provides the basis for assay methods to screen for inhibitors and activators of hydroxylation of ankyrin repeat containing proteins. In particular, the inventors' finding that the Asn 778 residue of p105 is hydroxylated by an asparagine hydroxylase provides the basis for assay methods designed to screen for inhibitors or promoters of this process. Any suitable method may be used to monitor for hydroxylation of an ankyrin repeat containing protein or analogue thereof. Assays may be carried out to monitor directly for hydroxylation of the relevant asparagine residue or another position. Alternatively, assays may be carried out to monitor for depletion of co-factors and co-substrates. Alternatively, such assays may monitor the downstream effects of hydroxylation or indeed inhibition of hydroxylation of the ankyrin repeat containing protein, for example, by monitoring the interaction between the protein and another molecule in the same signalling pathway or transcription mediated by the ankyrin repeat containing protein. Assays are also provided for the identification of enhancers of the activity of the ankyrin repeat containing protein asparagine hydroxylase.

The substrate, enzyme and potential inhibitor compound may be incubated together under conditions which, in the absence of inhibitor provide for hydroxylation of an asparagine residue in the substrate, and the effect of the inhibitor may be determined by determining hydroxylation of the substrate. This may be accomplished by any suitable means. Small polypeptide substrates may be recovered and subjected to physical analysis, such as mass spectrometry or chromatography, or to functional analysis, such as the ability to bind to another protein in the same signalling pathway. Such methods are known as such in the art and may be practiced using routine skill and knowledge. Determination may be quantitative or qualitative. In both cases, but particularly in the latter, qualitative determination may be carried out in comparison to a suitable control, e.g. a substrate incubated without the potential inhibitor.

Inhibitor compounds which are identified in this manner may be recovered and formulated as pharmaceutical compositions.

The interaction between an ankyrin repeat containing protein and another signalling protein may typically be monitored for example by the use of fluorescence polarisation, homogenous time resolved fluorescence, use of antibodies selective for the substrate or the hydroxylated substrate product, surface plasmon resonance or mass spectrometric analysis. In the first instance, the fluorescence polarisation of a dye attached to the test polypeptide changes when an interaction occurs, the interaction being dependent on the hydroxylation state of the test polypeptide. In the second instance, a test polypeptide may be immobilised on a chip constructed such that binding events may be detected by a change in force exerted on the chip. "Native" or "soft ionisation" mass spectrometry can be used as an assay for hydroxylase activity; thus interactions between an ankyrin repeat protein, or fragment thereof, and another protein are observed by mass spectrometry, whereas upon hydroxylation, this interaction may be reduced or abrogated. Transcription and expression of genes known to be upregulated or down regulated by the ankyrin repeat containing protein can be monitored.

In alternative embodiments, reporter constructs may be provided in which promoters mediated by the signalling pathway involving the ankyrin repeat containing protein are provided operably linked to a reporter gene. Any suitable reporter gene could be used, such as for example enzymes which may then be used in colorometric, fluorometric, fluorescence resonance or spectrometric assays.

Typically the 2-oxoglutarate dependent oxygenase and the substrate are contacted in the presence of a co-substrate, such as 2-oxoglutarate (2-OG) or dioxygen. Alternative co-substrates which substitute for 2-OG may also be used. The hydroxylase activity of the 2-OG dependent oxygenase may be determined by determining the turnover of the co-substrate. This may be achieved by determining the presence and/or amount of reaction products, such as hydroxylated substrate or succinic acid. The amount of product may be determined relative to the amount of substrate. The product measured may be hydroxylated substrate. For example, the extent of hydroxylation may be determined by measuring the amount of hydroxylated substrate, succinate or carbon dioxide generated in the reaction, or by measuring the depletion of 2-OG or dioxygen. Methods for monitoring each of these are known in the scientific literature.

Activity may be determined by monitoring other reporter molecules. For example, binding of substrate to the 2-OG oxygenase, such as to the active site of the 2-OG oxygenase, may be monitored.

Asparagine hydroxylase activity may be determined by determining the turnover of said 2-OG to succinate and $CO_2$, as described in Myllyharju J. et al. EMBO J. 16 (6): 1173-1180 (1991) or as in Cunliffe C. J. et al. Biochem. J. 240 617-619 (1986), or other suitable assays for $CO_2$, bicarbonate or succinate production.

Unused 2-OG may be derivatised by chemical reagents, exemplified by but not limited to hydrazine derivatives and ortho-phenylene diamine derivatives, to give indicative chromophores or fluorophores that can be quantified and used to indicate the extent of hydroxylation of the test polypeptide. Dissolved oxygen electrodes, exemplified by but not limited to a "Clarke-type" electrode or an electrode that uses fluorescence quenching, may be used to follow the consumption of oxygen in an assay mixture, which can then be used to indicate the extent of hydroxylation of the test polypeptide in an analogous manner to the above.

Alternatively, the end-point determination may be based on conversion of the substrate (including synthetic and recombinant peptides) into detectable products. Peptides may be modified to facilitate the assays so that they can be rapidly carried out and may be suitable for high throughput screening.

For example, reverse phase HPLC (using, for example, a C-4 octadecylsilane column), as exemplified herein, may be used to separate starting synthetic peptide substrates from the asparagine hydroxylated products, as the latter have a shorter retention time in the column. Modifications of this assay or alternative assays for hydroxylase activity may employ, for example, mass spectrometric, spectroscopic, and/or fluorescence techniques as are well known in the art (Masimirembwa C. et al. Combinatorial Chemistry & High Throughput Screening (2001) 4 (3) 245-263, Owicki J. (2000) J. Biomol. Screen. 5 (5) 297-305, Gershkovich A et al. (1996) J. Biochem. & Biophys. Meths. 33 (3) 135-162, Kraaft G. et al. (1994) Meths. Enzymol. 241 70-86). Fluorescent techniques may employ versions of the substrate modified in such as way as to carry out or optimise spectroscopic or fluorescence assays.

For example, the substrate may be immobilised, e.g. on a bead or plate, and hydroxylation of the appropriate residue detected using an antibody or other binding molecule which binds the substrate with a different affinity when an asparagine is hydroxylated from when the residue is not hydroxylated. Such antibodies may be obtained by means of standard techniques which are well known in the art.

Binding of a molecule which discriminates between the hydroxylated and non-hydroxylated form of an ankyrin repeat substrate may be assessed using any technique available to those skilled in the art, which may involve determination of the presence of a suitable label.

Assay methods of the present invention may also take the form of an in vivo assay. The in vivo assay may be performed in a cell line such as a yeast strain in which the relevant polypeptides or peptides are expressed from one or more vectors introduced into the cell.

The assays may be carried out using cell based, organ based or whole animal assays conducted in vivo. Such assays may utilize the endogenous expression of the 2-OG oxygenase or substrate. In other forms of the invention, upregulation of specific endogenous 2-OG oxygenase may be achieved by stimulators of the expression thereof. Such stimulators may be growth factors or chemicals that upregulate specific 2-OG oxygenases. In another form of the invention, nucleotide constructs may be introduced into cells or transgenic animals to increase production of one or more specific 2-OG oxygenase. Alternatively nucleotide constructs may be introduced into cells so as reduce or abrogate expression of one or more specific 2-OG oxygenase. Appropriate methods that include but are not limited to homologous recombination, antisense expression, ribozyme expression and RNA interference are outlined herein and known by those skilled in the art.

Tissue culture cells, organs, animals and other biological systems, obtained by the aforementioned forms of the invention, may be used to provide a further source of a 2-OG oxygenase, or may be used for the assay, or especially comparative assay, of the activity of test substances may inhibit, augment, block or otherwise modulate the activity of specific 2-OG oxygenase.

The activity of the 2-OG oxygenase may be assayed by any of the aforementioned methods or by cell, tissue, or other assays conducted in vivo that measure the effects of altered activity of the 2-OG oxygenase, either directly or indirectly.

An ankyrin repeat, or fragment thereof may be fused to a further polypeptide and used as a substrate for a 2-OG dependent oxygenase. Hydroxylase activity of the 2-OG dependent oxygenase may regulate the activity of the fusion peptide. Accordingly a further form of the invention provides for the assay of the activity of a fusion polypeptide.

The hydroxylation of the ankyrin substrate may, for example, be determined using a novel assay as described in Example 8 using the 2-OG oxygenase, factor inhibiting hypoxia-Inducible Factor (FIH-1). The reaction of FIH with a glutathione-S-transferase tagged fragment of the HIF transactivation domains (residues 786-826) has been previously described in which alternative assays including that employing detection of radioactive carbon dioxide were employed. The new assay procedure gives the same results as the previously used assay but is a safer and more efficient alternative.

In order to assay the consumption of 2-OG by FIR (and thus measure its catalytic activity), the inventors have developed derivatisation process whereby the 2-OG would form a fluorescent product with ortho-phenylenediamine OPD, or other suitable derivatisation reagent, whereas the succinate, or other products, did not.

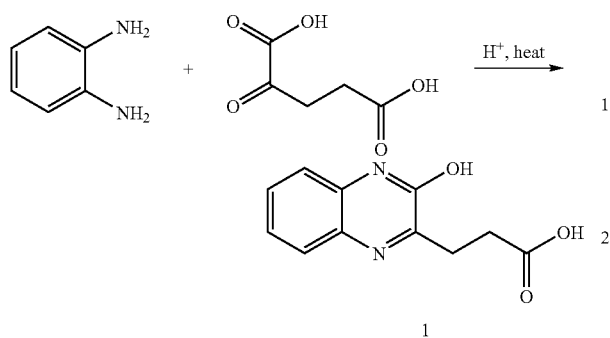

The fluorescent product of the reaction of OPD with the α-ketoacid motif of 2OG to give 3-(2-Carboxyethyl)-2(1H)-quinoxalinone is illustrated above and can be readily detected by standard equipment such as that manufactured by for example Molecular Devices, Tecan, BMG Labtechnologies, Jasco and Perkin Elmer and there is extensive precedent demonstrating that the production of fluorescent products can be used in high-throughput screens (e.g. those employing 96 well plate technology).

Further, there is extensive precedent demonstrating that the nature of the fluorescent product can be tuned by modifying the nature of the derivatisation reagent used. For example, the sensitivity of the method may be increased by using either 1,2-dimethoxy-4,5-diaminobenzene, or 1,2-methylenedioxy-4,5-diaminobenzene (Mühling et al. Journal of Chromatography B 2003 383-392, Nakamura et al. Chem. Pharm. Bull. 1987 687-692).

Thus this new assay for the consumption of 2-OG may be used to measure catalysis by 2-OG oxygenases such as FIH and the HIF prolyl hydroxylases, human enzymes such as AlkB, phytanoyl CoA hydroxylase, trimethyllysine hydroxylase, γ-butyrobetaine hydroxylase and collagen prolyl hydroxylase, enzymes in plant pathogens such as carbapenem synthase, and enzymes in antibiotic producing organisms such as deacetoxycephalosporin C synthase and clavaminic acid synthase. The new assay is safer and less complex than the existing procedure based on the release of radioactive $CO_2$. The new assay does not involve the release of gas (which is another drawback of the radioactive 2-OG method) from the assay vessel, or the use of radioactive isotopes. This assay procedure also lends itself to the high-throughput e.g. 96-, 384-, or 1536-well plate formats. It is suitable for use in assays for other types of 2-oxoacid utilising enzymes.

Selectivity

It may also be advantageous to modulate ankyrin repeat protein asparagine hydroxylase activity selectively, as a single target, or in selected hydroxylase groups as well as an entire family. Agents which modulate ankyrin repeat protein asparagine hydroxylase activity are therefore preferably selective or specific, i.e. they have an increased or enhanced effect on a ankyrin repeat protein asparagine hydroxylase relative to other hydroxylases which hydroxylate an asparagines residue in an ankyrin repeat protein.

It is also recognised that in some circumstances it may be advantageous to selectively inhibit FIH and one or more of the aforementioned enzymes, in particular one or more of the HIF prolyl hydroxylase isoforms. Further, in inhibiting some of the above enzymes it may be advantageous not to inhibit FIH and the methods can be used in a method for discovering PHD inhibitors that are not inhibitors of FIH. The invention provides for the use of such selective inhibitors in the manufacture of a medicament for the treatment of a condition associated with altered, i.e. enhanced or reduced, ankyrin protein activity.

Activities against different enzymes may be compared to detect inhibitors that are selective for a particular 2-OG oxygenase or a particular form of a 2-OG oxygenase including but not limited to FIH, AlkB, procollagen prolyl and lysyl hydroxylases, Mina53, the phosphatidylserine receptor, 2-OG oxygenases that have been characterised as JmjC proteins, according to the SMART database, and/or any of the PHD enzymes including PHD 1, PHD 2 and PHD3.

Activities of a given 2-OG oxygenase on different substrates may be compared to determine whether an inhibitor is selective for the activity of the 2-OG oxygenase on a single substrate, or group of substrates. For example, to determine whether an inhibitor can selectively inhibit hydroxylation of HIF by FIH but not of an ankyrin, or vice versa. The single substrate may, for example, be a HIF isoform.

Test Compounds

Compounds which may be screened using the assay methods described herein may be natural or synthetic chemical compounds used in drug screening programmes. Extracts of plants, microbes or other organisms, which contain several characterised or uncharacterised components may also be used.

Combinatorial library technology (including solid phase synthesis and parallel synthesis methodologies) provides an efficient way of testing a potentially vast number of different substances for ability to modulate an interaction. Such libraries and their use are known in the art, for all manner of natural products, small molecules and peptides, among others. The use of peptide libraries may be preferred in certain circumstances.

Potential inhibitor compounds may be polypeptides, small molecules such as molecules from commercially available combinatorial libraries, or the like. Small molecule compounds which may be used include 2-OG analogues, or ankyrin repeat analogues, or those that incorporate features of both 2-OG and an ankyrin repeat, which inhibit the action of the enzyme.

Potential promoting agents may be screened from a wide variety of sources, particularly from libraries of small compounds which are commercially available. Oxygen-containing compounds may be included in candidate compounds to be screened, for example 2-OG analogues.

A test compound which increases, potentiates, stimulates, disrupts, reduces, interferes with or wholly or partially abolishes asparagine hydroxylation of the substrate and which may thereby modulate activity, may be identified and/or obtained using the assay methods described herein.

Agents which increase or potentiate asparagine hydroxylation, may be identified and/or obtained under conditions which, in the absence of a positively-testing agent, limit or prevent hydroxylation. Such agents may be used to potentiate, increase, enhance or stimulate the asparagines hydroxylase activity of a 2-OG oxygenase.

In various aspects, the present invention provides an agent or compound identified by a screening method of the invention to be a modulator of ankyrin repeat containing protein asparagine hydroxylation e.g. a substance which inhibits or reduces, increases or potentiates the asparagine hydroxylase activity of a 2-OG oxygenase on an ankyrin repeat containing protein.

Following identification of a modulator, the substance may be purified and/or investigated further (e.g. modified) and/or manufactured. A modulator may be used to obtain peptidyl or non-peptidyl mimetics, e.g. by methods well known to those skilled in the art and discussed herein. A modulator may be modified, for example to increase selectively, as described herein. It may be used in a therapeutic context as discussed below.

Compounds which modulate 2-OG oxygenases may be useful as agents of the invention, or may be used as test substances in an assay of the invention. Compounds which modulate 2-OG oxygenases, and families of such compounds, are known in the art, for example in Aoyagi et al. (2002) Hepatology Research 23 (1): 1-6, Aoyagi et al. (2003) Free Radical Biology and Medicine 35:410 Suppl. 1, Philipp et al. (2002) Circulation 106 (19): 1344 Suppl. S, Ivan et al. (2002) PNAS USA 99 (21): 13459-13464, Nwogu et al. (2001) Circulation 104 (18): 2216-2221, Myllyharju and Kivirikko (2001) Ann Med 33 (1): 7-21, Ohta et al. (1984) Chemical and Pharm Bulletin 32 (11): 4350-4359, Franklin et al. (2001) Biochem J. 353: 333-338, Franklin (1997) Int J. Biochem Cell Biol 29 (1): 79-89, Dowell et al. (1993) Eur J Med Chem 28 (6): 513-516, Baader et al. (1994) Biochem J. 300: 525-530, Baader et al. (1994) Eur J Clin Chem and Clin Biol 32 (7): 515-520, Bickel et al. (1998) Hepatology 28 (2): 404-411, Bickel et al. (1991) J. Hepatology 13: S26-S34 Suppl. 3, U.S. Pat. No. 6,200,974, U.S. Pat. No. 5,916,898, US Patent Applications 2003-0176317, 2003-0153503 and 2004-0053977, WO 02/074981, WO 03/080566, WO 04/035812, Cunliffe et al. (1992) J. Med. Chem. 35:2652-2658, Higashide et al. (1995) J. Antibiotics 38:285-295, Cunliffe et al. (1986) Biochem. J. 239(2):311-315, Franklin et al. (1989) Biochem. J. 261(1):127-130, Friedman et al (2000) PNAS USA 97(9):4736-4741, Wu et al. (1999) J. Am. Chem. Soc. 121(3): 587-588, DE-A-3818850, Wang et al. (2001) Biochemistry US: 15676-15683 and Lerner et al. (2001) Angew Chem. Int. Edit. 40:4040-4041.

Some of these compounds, particularly those described in WO 02/074981 and WO 03/080566, generally possess the formula:

where the group $R^1$ is capable of forming an electrostatic interaction with the sidechain of the arginine residue which, together with other residues, binds the 5-carboxylate of 2-oxoglutarate during catalysis, A*B is a chain of two atoms which are, independently, carbon, oxygen, nitrogen or sulphur, which chain can be functionalised, y is 0 or 1 and C*D is a chain of two atoms which are, independently, carbon, oxygen, nitrogen, or sulphur, which chain can be functionalised, A, B, C and D being linked to one another by a single and/or double and/or triple bond such that when y is 0 or 1 at least one of the atoms of which is capable of chelating with a metal group and when y is 1 said chain is attached to $R^2$ which is capable of chelating with a metal group. Generally at least one of A, B, C and D is not carbon. Typical chains include C—N—C—C and C—O—C—C and C—C—C—O. The chain atoms can form part of a ring.

Other suitable agents possess the following formulae (A) to (F)

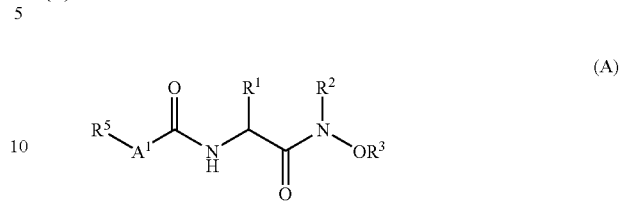

where each of $R^1$ and $R^5$ is independently H, OH, SH, a branched or straight $C_1$ to $C_6$ alkyl chain optionally containing 1 or more e.g. 2 N, S, O or P chain atoms, especially methyl, which can be functionalised, any amino acid side chain, such as alanine, phenylalanine, valine and glutamic acid, a 4 to 7 membered heterocyclic ring optionally containing 1 or 2 N, S, O or P atoms or a 5 or 6 membered aromatic ring, optionally containing 1 or 2 N, O or S atoms which may be fused to another ring or a said alkyl chain substituted by a said aromatic ring, such as aryloxy alkyl, $A^1$ is $CH_2$ or O, and each of $R^2$ and $R^3$ is independently be H, OH, a branched or straight $C_1$ to $C_6$ alkyl chain optionally containing 1 or more e.g. 2 N, S, O or P chain atoms which can be functionalised, optionally with 1, 2, 3, 4 or 5 halo substitutions, a 4 to 7 membered heterocyclic ring optionally containing 1 or 2 N, S, O or P atoms, or a 5 or 6 membered aromatic ring, optionally containing 1 or 2 N, O or S atoms which may be fused to another ring or a said alkyl chain substituted by a said aromatic ring,

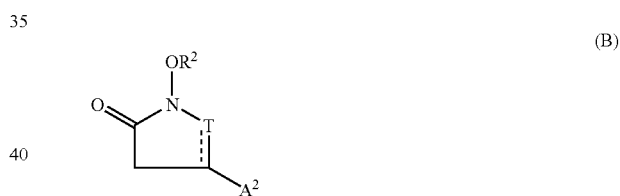

wherein $R^2$ is as defined above, ---is a single bond and T is $CH_2$ or C=O, or ---is a double bond and T is CH; $A^2$ is H or —XCO$_2$R$^4$; X is a single bond or a branched or straight $C_1$ to $C_6$ alkyl chain, optionally containing 1 or more e.g. 2 N, S, O or P chain atoms and optionally substituted by e.g. halo, OH, NHR$^2$ or NHCOR$^4$ where $R^2$ and $R^4$ are as defined above and $R^4$ represents H, a branched or straight chain $C_1$ to $C_6$ alkyl group optionally containing 1 or more e.g. 2 N, S, O or P chain atoms, a 4 to 7 membered heterocyclic ring, optionally containing 1 or 2 N, S, O or P atoms, or a 5 or 6 membered aromatic ring, optionally containing 1 or 2 N, O or S atoms, which may be fused to another ring, or a salt thereof,

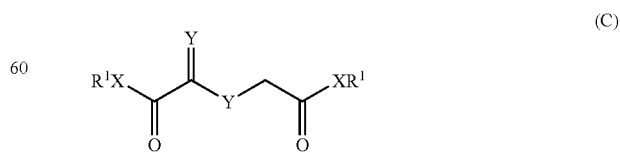

where each X which may be the same or different is NH, NR", where R" is OH, a branched or straight $C_1$ to $C_6$ alkyl chain optionally containing 1 or more e.g. 2 N, S, O or P chain atoms which can be functionalised, or O i.e. $XR^1$ is typically OH or O-alkyl having a branched or straight $C_1$ to $C_6$ alkyl chain, especially MeO, each Y, which may be the same or different, is O or S and each $R^1$, which may be the same or different, is as defined above,

where m is 0 or 1, Q represents $(R^1R^6)_xZ$ where x is 0, 1 or 2, $R^1$ is as defined above and $R^6$ is as defined for $R^1$, and Z is $P=O(OH)_2$, $B(OH)_2$ or $SO_3H$, or a salt thereof, typically a sodium salt, or

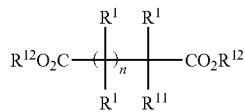

where each $R^1$, which are the same or different, is as defined above; $R^{11}$ represents OH or $R^{10}NH$ where $R^{10}$ is HO, $R^1CO$ or $HOOC(X)_x$ wherein $R^{11}$ is as defined above, x is 0 or 1 and X is $R^1R^1C$ wherein each $R^1$, which are the same or different, is as defined above; or $R^{10}$ is an amino acid residue $H_2N$ $(R^1R^1C)CO$— wherein each $R^1$, which are the same or different, is as defined above; n is 1 or 2 and $R^{12}$ is H or straight or branched $C_1$ to $C_6$ alkyl; or a salt thereof. Typically X is $CH_2$ or CHOH. Another aspect of the invention concerns analogues of 2-OG that act as improved (relative to 2-OG) co-substrates for the 2-OG dependent oxygenases. Such a compound is 3-fluoro 2-OG. Assays in which this compound replaces 2-OG demonstrate a higher level of asparagine hydroxylation than observed when using 2-OG under analogous conditions.

These analogues possess the formula:

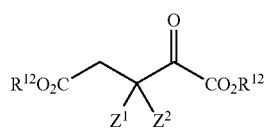

wherein each of $Z^1$ and $Z^2$ is independently hydrogen, SH or an electron withdrawing group such as halogen, preferably fluorine, or alkoxy such as methoxy, and $R^{12}$ is as defined above, or a salt thereof. Preferably one of $Z^1$ and $Z^2$ is hydrogen and the other is fluorine (3-F-2-OG).

The said alkyl groups and chains are typically functionalised by alcohol, fluorine, thiol, a carboxylic acid, phosphonic or phosphinic acid, sulphonic acid or other chelating group, in the case of the chains typically via an alkyl group.

In the formulae described herein, a branched or straight $C_1$ to $C_6$ alkyl chain may be a methyl, ethyl, propyl, butyl, isobutyl, tert-butyl, pentyl, neopentyl, tert-pentyl or a primary, secondary or tertiary hexyl group. Hetero atoms such as O, S, N and P may replace one or more of the carbon atoms. Preferably the alkyl groups are methyl, the preferred heterocyclic rings are pyrrolidine and tetrahydropyran and the preferred aromatic rings are benzene, naphthalene and pyridine.

Typically, each of $R^1$ and $R^5$ is independently H, OH, a branched or straight $C_1$ to $C_6$ alkyl chain optionally containing 1 or more N, S, O or P chain atoms, which can be functionalised, any amino acid side chain, a 4 to 7 membered heterocyclic ring optionally containing 1 or 2 N, S, O or P atoms or a 5 or 6 membered aromatic ring, optionally containing 1 or 2 N, O or S atoms which may be fused to another ring or a said alkyl chain substituted by a said aromatic ring.

Typically, $A^1$ is $CH_2$.
Typically, $A^2$ is $—XCO_2R^4$.
Typically, $R^{11}$ represents $R^{10}NH$ where $R^{10}$ is $R^1CO$ or $HOOC(X)_x$ wherein $R^1$ is as defined above, x is 0 or 1 and X is $R^1R^1C$ wherein each $R^1$, which are the same or different, is as defined above; or $R^{10}$ is an amino acid residue $H_2N$ $(R^1R^1C)$ CO— wherein each $R^1$, which are the same or different, is as defined above.

Typically, each of $Z^1$ and $Z^2$ is independently hydrogen or an electron withdrawing group.

Typically, in the compounds of formula (F), $R^{12}$ is H. Alternatively, $R^{12}$ may be straight or branched $C_1$ to $C_6$ alkyl.

The compounds of formula (A) are hydroxamates. Preferred compounds include those where $R^5$ is aryloxyalkyl, especially oxyloxymethyl such as phenyloxymethyl or phenylalkyloxymethyl, especially benzyloxymethyl or substituted benzyloxymethyl such as p-hydroxy benzyloxymethyl and/or where $R^2$ and/or $R^3$ is $HOCH_2$.

Typical compounds include N-phenoxy-acetyl-(L)-alanine-hydroxamide (Is41) and the corresponding (D) isomer (Is43) as well as the corresponding tyrosine derivatives (Is44 and 45) and L- and D-phenylglycine derivatives (Is46 and 47), along with benzo hydroxamic acid and N-phenoxyacetyl-D-phenylalanine hydroxamic acid (Is42).

These compounds can generally be prepared following the method of Walter et al., Tetrahedron 1997, 53, 7275-7290 and Biorg. Chem. 1999, 27, 35-40.

The compounds of formula (B) are cyclic hydroxamates. Preferred compounds are those where X is a single bond or methyl and/or $R^2$ is H or phenylalkyl, especially benzyl and/or $R^4$ is H or methyl. Typical compounds include (1-hydroxy-2,5-dioxo-pyrrolidin-3-yl) acetic acid (Is52), (1-hydroxy-2,5-dioxo-pyrrolidin-3-yl) carboxylic acid (ANU 2) and its N-benzoyloxy derivative (ANU 1) along with (1-benzyloxy-2,5-dioxo-pyrrolidin-3-yl) acetic acid (Is50) and the corresponding methyl ester (Is64), and N-hydroxy succinimide (C1). Note that Is52 ($R^2$=H, T=C=O, X=$CH_2$ $R^4$=H) is highly active reflecting its structural analogy with 2-oxoglutarate. These compounds can be prepared using the general procedure of Schlicht et al. (U.S. Pat. No. 4,446,038).

The compounds of formula (C) are analogues of 2-oxoglutarate or oxalyl derivatives of hydroxyacetate and mercapto acetic acid. Preferred compounds include those where X is O and/or $R^1$ is H or methyl. Typical compounds include dimethyl oxalylglycolate (Is10) as well as its free acid (Is14) and dimethyl oxalylthioglycolate (Is11). These compounds can be prepared following Franklin et al., J. Med. Chem. 1992, 35, 2652-2658 or Kwon et al., J. Am. Chem. Soc. 1989, 111, 1854-1860.

The compounds of formula (D) are carboxylic acids which possess a phosphonic, sulphonic or boronic acid group as well as salts of these. Typically $R^1$ and $R^6$ are hydrogen. Preferred compounds include the phosphoric acids where x is 0, 1 or 2 (C3, 4 and 5, respectively) as well as disodium 3-sulphopropionate (Is63) and its free acid, and 3-borono-propionic acid (Is62).

The compounds of formula (E) are N-acylated amino acids or polycarboxylic acids. Typical compounds are those where $R^1$ is H, and/or $R^{12}$ is H or ethyl. When $R^{11}$ represents $R^{10}NH$ the compounds are typically dipeptides such that $R^{10}$ is an acyl group of a natural amino acid such as glycine. Typical preferred such compounds include Asp-Gly (C18), cyclo (Asp-Gly) (C19), beta-Asp-Gly (C20), Glu-Gly (C21) and Z-Glu-Gly (C22). Other typical compounds include those where $R^{10}$ is acetyl or benzoyl such as the N-acetylated derivatives of L-aspartic acid (C6) and of L-glutamic acid (C7) i.e. $R^{10}$ is acetyl and N-benzoylated derivatives of glutamic acid (C15 and Is90) i.e. $R^{10}$ is benzoyl. Other typical compounds include those where $R^{11}$ is —NHOH such as diethyl 2-(hydroxylamino)-glutarate (Is51 being the racemic form of this compound) and those where $R^{11}$ is OH such as 2-hydroxyglutaric acid (Is57). When $R^{11}$ is $HOOC(X)_x$, X is especially $CH^2$ or CHOH. The compounds are typically citric acid (C12), tricarballylic acid (C13) and succinic acid as well as the tri-methyl ester of ethane tricarboxylic acid (Is72).

The compounds of formula (F) are analogues of 2-oxoglutarate. Preferred compounds include 3-fluoro-2-oxoglutarate compounds (i.e. $Z^1$ is H and $Z^2$ is F) such as 3-fluoro-2-oxoglutaric acid (Is18) and the corresponding dimethyl ester (Is19).

The compounds which are acids can be present in the form of salts, such as sodium salts.

For therapeutic treatment, the compound may be used in combination with any other active substance, e.g. for anti-tumour therapy another anti-tumour compound or therapy, such as radiotherapy or chemotherapy.

Further compounds that may be used as 2-OG oxygenase inhibitors are disclosed in our co-pending UK Patent Application No. 0419128.4, which is incorporated herein by reference.

Ankyrin repeat proteins and analogues thereof, including fragments of such proteins and analogues may also be used as inhibitors of 2-OG oxygenase activity. Any of the substrates defined herein may be used as inhibitors, in particular as inhibitors of 2-OG oxygenase activity on non-ankyrin repeat containing substrates such as HIF. The analogue may typically be any of the ankyrin repeat containing proteins described herein but which lacks the asparagine residue that is hydroxylated by 2-OG oxygenases. The asparagines residue is typically substituted by another amino acid. The substitution is preferably conservative as indicated in the Table above.

Therapeutic Applications

An agent, such as a substance or composition, which is found to have the ability to affect the hydroxylase activity of a 2-OG dependent oxygenase on a substrate comprising an ankyrin repeat, or a fragment thereof, has therapeutic and other potential uses in a number of contexts. Agents which are selective inhibitors at a particular substrate or of a particular 2-OG oxygenase are particularly useful in therapeutic methods. For therapeutic treatment, such a compound may be used in combination with any other active substance, e.g. for anti-tumour therapy with another anti-tumour compound or therapy, such as radiotherapy or chemotherapy.

An agent identified using one or more primary screens (e.g. in a cell-free system) as having ability to modulate the asparagine hydroxylation activity of a 2-OG dependent oxygenase on a substrate comprising an ankyrin repeat or a fragment thereof may be assessed further using one or more secondary screens. A secondary screen may involve testing for an increase or decrease in the amount of ankyrin repeat protein activity, for example as manifest by the level of a target gene or process present in a cell in the presence of the agent relative to the absence of the agent.

Generally, an agent, compound or substance which is a modulator according to the present invention is provided in an isolated and/or purified form, i.e. substantially pure. This may include being in a composition where it represents at least about 90% active ingredient, more preferably at least about 95%, more preferably at least about 98%. Any such composition may, however, include inert carrier materials or other pharmaceutically and physiologically acceptable excipients, such as those required for correct delivery, release and/or stabilisation of the active agent. As noted below, a composition according to the present invention may include in addition to an modulator compound as disclosed, one or more other molecules of therapeutic use, such as an anti-tumour agent.

Products Obtained by Assays of the Invention

The invention further provides compounds obtained by assay methods of the present invention, and compositions comprising said compounds, such as pharmaceutical compositions wherein the compound is in a mixture with a pharmaceutically acceptable carrier or diluent. The carrier may be liquid, e.g. saline, ethanol, glycerol and mixtures thereof, or solid, e.g. in the form of a tablet, or in a semi-solid form such as a gel formulated as a depot formulation or in a transdermally administerable vehicle, such as a transdermal patch.

Hydroxylation modifies the biological effects of ankyrin repeat proteins, so modulating the extent of hydroxylation, for example by inhibiting FIH, has medicinal applications. Thus, the invention further provides a method of treatment which includes administering to a patient an agent which interferes with the hydroxylation of the asparagine target residue of ankyrin repeat containing protein. Such agents may include inhibitors of asparagine hydroxylase activity.

The therapeutic/prophylactic purpose may be related to the treatment of a condition associated with reduced or suboptimal or increased ankyrin repeat-containing protein levels or activity, or conditions which have normal ankyrin repeat containing protein levels, but where a modulation in ankyrin repeat-containing protein activity, such as an increase or decrease in ankyrin repeat-containing protein activity, is desirable.

Compounds which are known in the art to inhibit 2-OG oxygenase activity may be used to treat diseases associated with ankyrin repeat proteins.

The conditions that may be treated include:

(i) ischaemic conditions, for example organ ischaemia, including coronary, cerebrovascular and peripheral vascular insufficiency. The therapy may be applied in two ways; following declared tissue damage, e.g. myocardial infarction (in order to limit tissue damage), or prophylactically to prevent ischaemia, e.g. promotion of coronary collaterals in the treatment of angina;

(ii) cancer; HIFα is commonly up-regulated in tumour cells and has major effects on tumour growth and angiogenesis. This therapeutic application preferably requires a therapeutic agent selective for one or more HIF isoform compared to an ankyrin repeat protein;

(iii) inflammatory disorders;

(iv) immune disorders such as diabetes;

(v) anaemia and beta thalassemia.

Modulating ankyrin repeat-containing protein asparaginyl hydroxylase activity in a person, an organ, or a group of cells may be exploited in different ways to obtain a therapeutic benefit.

An agent of the invention may promote cell survival or proliferation and/or inhibit apoptosis (such as might be achieved by reducing interaction of p53 and ASPP1 or 2 or increasing interaction of p53 with iASPP or by reducing interaction of the tumour suppressor proteins p16 or p18 with cyclin dependent kinases). Such an agent is useful in the treatment of ischaemia, hypoxia or otherwise damaged tissues.

An agent of the invention may inhibit survival of tumour cells (such as might be achieved by promoting interaction of p53 and ASPP1 or ASPP2 or decreasing interaction of p53 with iASPP or by promoting interaction of the tumour suppressor proteins p16 or p18 with cyclin dependent kinases). Such an agent is active against cancerous tissues.

An agent of the invention may regulate inflammation and immunity (such as might be achieved by reducing or increasing the interaction between NFκB proteins such p105 and IκB-α and the p50/p65 transcriptional complex).

An agent of the invention which inhibits the activity of a 2-OG oxygenase may be useful in the treatment of anaemia (e.g. sickle cell anaemia) and beta thalassemia. Such an agent may act through the induction of haemoglobin F (HbF). HbF is believed to be induced by a factor which is deactivated by hydroxylation by a 2-OG oxygenase. Inhibiting the 2-OG oxygenase reduces that deactivation of the factor and hence leads to more HbF being produced.

An ankyrin-containing protein that is hydroxylated to give a residue not normally found in proteins may be prepared either in a post-translational process such as a process catalysed by a 2-OG oxygenase, or otherwise. Such a modified ankyrin containing protein may be used in the treatment of ischemia, cancer, inflammatory disorders and immune disorders. Hydroxylation is preferably at an asparaginyl residue.

Similarly, a structural analogue of a hydroxylated ankyrin containing protein may be used in the treatment of ischemia, cancer, inflammatory disorders and immune disorders.

A therapeutically effective amount of an agent is typically administered to a subject in need thereof. A therapeutically effective amount is an amount which ameliorates the symptoms of the condition or lessens the suffering caused to the subject by the condition.

Pharmaceutical Compositions

In various further aspects, the present invention thus provides a pharmaceutical composition, medicament, drug or other composition for such a purpose, the composition comprising one or more agents, compounds or substances as described herein, including inhibitors of asparagine hydroxylase activity on a ankyrin repeat containing protein; the use of such an composition in a method of medical treatment; a method comprising administration of such a composition to a patient, e.g. for treatment (which may include preventative treatment) of a medical condition as described above; use of such an agent compound or substance in the manufacture of a composition, medicament or drug for administration for any such purpose, e.g. for treatment of a condition as described herein; and a method of making a pharmaceutical composition comprising admixing such an agent, compound or substance with a pharmaceutically acceptable excipient, vehicle or carrier, and optionally other ingredients.

In one embodiment the method for providing a pharmaceutical composition may typically comprise:

(a) identifying an agent by an assay method of the invention; and (b) formulating the agent thus identified with a pharmaceutically acceptable excipient.

The pharmaceutical compositions of the invention may comprise an agent, polypeptide, polynucleotide, vector or antibody according to the invention and a pharmaceutically acceptable excipient.

The agent may be used as sole active agent or in combination with another agent or with any other active substance, e.g. for anti-tumour therapy another anti-tumour compound or therapy, such as radiotherapy or chemotherapy.

Whatever the agent used in a method of medical treatment of the present invention, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

An agent or composition may be administered alone or in combination with other treatments, either simultaneously or sequentially dependent upon the condition to be treated, e.g. as described above.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. In particular they may include a pharmaceutically acceptable excipient. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations. Examples of techniques and protocols mentioned above can be found in Remington's Pharmaceutical Sciences, 16th edition, Osol, A. (ed), 1980.

The substance or composition may be administered in a localised manner to a particular site or may be delivered in a manner in which it targets particular cells or tissues, for example using intra-arterial stent based delivery.

Targeting therapies may be used to deliver the active substance more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

In a further embodiment the invention provides for the use of an agent of the invention in the manufacture of a medicament for the treatment of a condition associated with increased or decreased ankyrin repeat protein levels or activity. The condition may, for example, be selected from the group consisting of ischaemia, cancer, and inflammatory and immune disorders.

The following Examples illustrate the invention.

EXAMPLE 1

Experimental Details

Yeast Two-hybrid Library Screening

A HUVEC cDNA library (constructed in pPC86) was screened by co-transformation with FIH bait cloned into pDBLeu (Invitrogen) using the Y190 yeast strain and standard protocols. A human testis cDNA library was also screened with FIH bait. This was performed by yeast mating utilising strain AH109 containing FIH cloned into pAS1-

CYH2 and a commercial human testis cDNA library (constructed in pACT2) pre-transformed in strain Y187 (BD Biosciences).

Immunoprecipitation and Immunoblotting

HeLa and U2OS cell extracts were prepared in Igepal lysis buffer (100 mM NaCl, 20 mM Tris —HCl pH 7.6, 5 mM $MgCl_2$ 0.5% Igepal CA630 containing "Complete" protease inhibitor, Roche Molecular Biochemicals). To analyse the p105/FIH interaction, p105 immunoprecipitations were performed using an antibody directed against the C-terminal region of p105 (Salmeron et al., J. Biol. Chem. (2001) 276 22215-22222). Following SDS-PAGE, immunoprecipitated proteins were transferred on to IMMOBILON™ P membrane (Millipore) and processed for immunoblotting with a monoclonal anti-FIH antibody (prepared in host laboratory). To analyse the IκBα/FIH interaction, FIH immunoprecipitations were performed using polyclonal FIH antiserum (prepared in host laboratory) and immunoblotted with anti-IκBα antibody (clone 10b, Prof R. Hay, St. Andrew's University).

Cloning, Bacterial Expression and Purification of p105 and IκB-α

Plasmid corresponding to the ankyrin repeat domain (ARD) of p105, (amino acid residues 537-809) downstream of glutathione S-transferase (GST) (Bell et al. Mol.Cell.Biol. (1996) 16 6477-6485) was transformed into *E.coli* BL21 (DE3) and grown at 37° C. in 2TY medium supplemented with 100 ug/ml ampicillin. Once the $OD_{600}$ reached 0.8 the temperature was reduced to 28° C. and IPTG was added to 0.5 mM. Cells were harvested 4 hrs later by centrifugation. The GST-tagged protein was purified using standard protocols with Glutathione SEPHAROSE™ 4B resin (Amersham Biosciences). The tag was cleaved where necessary using thrombin. A second purification step using the Glutathione SEPHAROSE™ 4B resin yielded protein of >90% purity by SDS-PAGE analysis. The GST p105 L668K mutant was made using the Quickchange system (Stratagene) and the following primers (forward: GCCTGCCATGTTTGAAGCT-GCTGGTGGCCGC (SEQ ID NO:6) and reverse: GCGGC-CACCAGCAGCTTCAAACATGGCAGGC (SEQ ID NO:7)).

The iκB-α/pGEX-2T construct (Jaffray et al. Mol. Cell. Biol. (1995) 15 2166-2172) was transformed into *Escherichia coli* BL21(DE3) cells (Stratagene) and the recombinant protein expressed and purified essentially as described above for the p105 fragments.

FIH Assays

The peptides shown in Table 1 were tested as potential substrates with purified FIH. The proposed sites of asparaginyl hydroxylation are highlighted in the Table.

| Name | Sequence | SEQ ID NO. |
|---|---|---|
| p105 | SLPCLLLLVAAGADV<u>N</u>AQEQK | 2 |
| IkappB-alpha | YLGIVELLVSLGADV<u>N</u>AQEPC | 1 |
| FEM-1 | NALVTKLLLDCGAEV<u>N</u>AVDNE | 3 |
| CAD | DESGLPQLTSYDCEV<u>N</u>API | 11 |
| Bcl-3 | SLSMVQLLLQHGANV<u>N</u>AQMY | 12 |
| P19-INK4d | FLDTLKVLVEHGADV<u>N</u>VPDG | 13 |
| GABPbeta | HASIVEVLLKHGADV<u>N</u>AKDM | 14 |
| Tankyrase-1/2 | NLEVAEYLLEHGADV<u>N</u>AQDK | 15 |
| 2-5A-d-R | VEVLKILLDEMGADV<u>N</u>ACDN | 16 |
| Gankyrin/p28-II | RDEIVKALLGKGAQV<u>N</u>AVNQ | 17 |
| Myotrophin | QLEILEFLLLKGADI<u>N</u>APDK | 18 |
| M110 | YTEVLKLLIQAGYDV<u>N</u>IKDY | 19 |
| FGIF | NTRVASFLLQHDADI<u>N</u>AQTK | 20 |

In addition p105 ARD and IkappaB-alpha were also assayed as substrates. The substrates were assayed for decarboxylation of 2OG using radiolabelled 2OG as reported in Hewitson et al., J. Biol. Chem. (2002) 277 26351-26355. FIH was incubated with 5 mmols of each substrate together with ascorbate, 2OG, Fe and catalase in 50 mM Tris-HCl, pH 7.5 at 37° C. for 20 minutes.

Expression and Purification of p105 L668K/R870A from 293T Cells

For expression in 293T cells, pcDNA 3.1/GS plasmid containing p105 with a C-terminal PK-epitope tag (Invitrogen) was modified using the Quickchange system (Stratagene). The L668K mutation was made using primers described earlier. The R870A mutation with primers (forward: TCTGGGGGTACAGTCGCAGAGCTGGTGGAGGC, SEQ ID NO:8) and (reverse: GCCTCCACCAGCACTGC-GACTGTACCCCCAGA, SEQ ID NO:9). The resulting p105 L668K/R870A plasmid was transiently transfected into 293T cells (5 μg DNA / 15 cm plate) using FUGENE™ 6 (Roche Molecular Biochemicals). 36h post-transfection, cells were lysed in 2 ml (100 mM NaCl, 0.5% Igepal CA630, 20 mM Tris-HCl pH7.6, 5 mM $MgCl_2$, containing "Complete" protease inhibitor (Roche Molecular Biochemicals) / 15 cm plate. Lysates were then centrifuged at 10,000×g for 15 min at 4° C. The lysate was then incubated with 30 μl anti-PK agarose conjugate (anti-V5, clone V5-10 Agarose conjugate, Sigma) on a rotator for 90 min at 4° C. Beads were then washed 6 times in lysis buffer and purified protein resolved by SDS-PAGE.

Tryptic Digests

For in-gel digests, gel pieces were incubated with 20 mM trypsin in 20 mM ammonium bicarbonate and incubated at 37° C. for 16 hrs. For solution digests, after incubation with FIH under standard assay conditions, a 25 μM sample of substrate was removed from the assay, combined with 2.5 μM trypsin in 25 mM ammonium bicarbonate and incubated at room temperature for 8 hours.

Mass Spectrometric Analyses

Both in vitro and in vivo produced p105 samples were analysed using an Ettan™ MALDI-ToF Pro mass spectrometer in reflectron mode (Amersham Biosciences) with ANG III and hACTH peptides as internal standards. Tryptic fragments of in vitro produced IkappaB-alpha were analysed using a MALDI-TOF 2T mass spectrometer (MICRO-MASS™) in reflectron mode using Substance P, hACTH and insulin (B chain, oxidized) calibration standards.

LC-MS

A Jupiter C4 HPLC column (15 cm×4.6 mm) was used to purify the substrate peptides following incubation with FIH using a linear gradient of 5-95% acetonitrile/0.05% formic acid at a flow rate of 1 ml/min. The eluate from the column was analysed by a MICROMASS™ ZMD quadrupole mass spectrometer in positive mode.

NMR

Both the FEM-1 and IkappaB-alpha peptides (2 mg) were incubated with FIH under standard assay conditions. Peptides were purified from the assay mixture using a Jupiter C4 HPLC column (15 cm×4.6 mm) with a linear gradient of 5-95% acetonitrile. Peptides were lyophilised and then redissolved in neat $^2H_2O$ containing 1,4-dioxan as the internal chemical shift reference ($^1H$ 3.750, $^{13}C$ 67.80 p.p.m.). NMR spectra were obtained using a Bruker Avance DRX500 equipped with an inverse-broadband pulsed-field gradient probe.

EXAMPLE 2

Identification of New Substrates for FIH

FIH was first identified in a yeast two-hybrid screen for HIF-1α interacting proteins (Mahon et al. Genes Dev (2001)) indicating that FIH enzyme-substrate interactions can be detected with this system. A HUVEC cDNA library was screened with FIH as bait. From this, 115 positive clones, representing 9 independent proteins were obtained. Of these, one corresponded to the HIF-1α substrate (residues 520-826) verifying the integrity of the screen whilst two ankyrin repeat domain-containing proteins were isolated: 61 clones corresponding to p105 (the minimal domain being residues 642-969) and 6 clones corresponding to UACA (uveal autoantigen with coiled-coil domains and ankyrin repeats, minimal domain residues 140-1416). Both of the ankyrin repeat domain-containing proteins contained a candidate site of asparaginyl hydroxylation (by comparison with the HIF-1α substrate sequence).

Additionally, a human testis cDNA library was also screened with FIH bait. From this 3 positive clones representing 3 proteins were obtained. One clone corresponded to the ankyrin repeat domain-containing protein Fem-1b (residues 456-627) that also contained a candidate site of asparaginyl hydroxylation.

EXAMPLE 3

In vivo Interaction Between FIH and p105/IκBα

Figure 2:
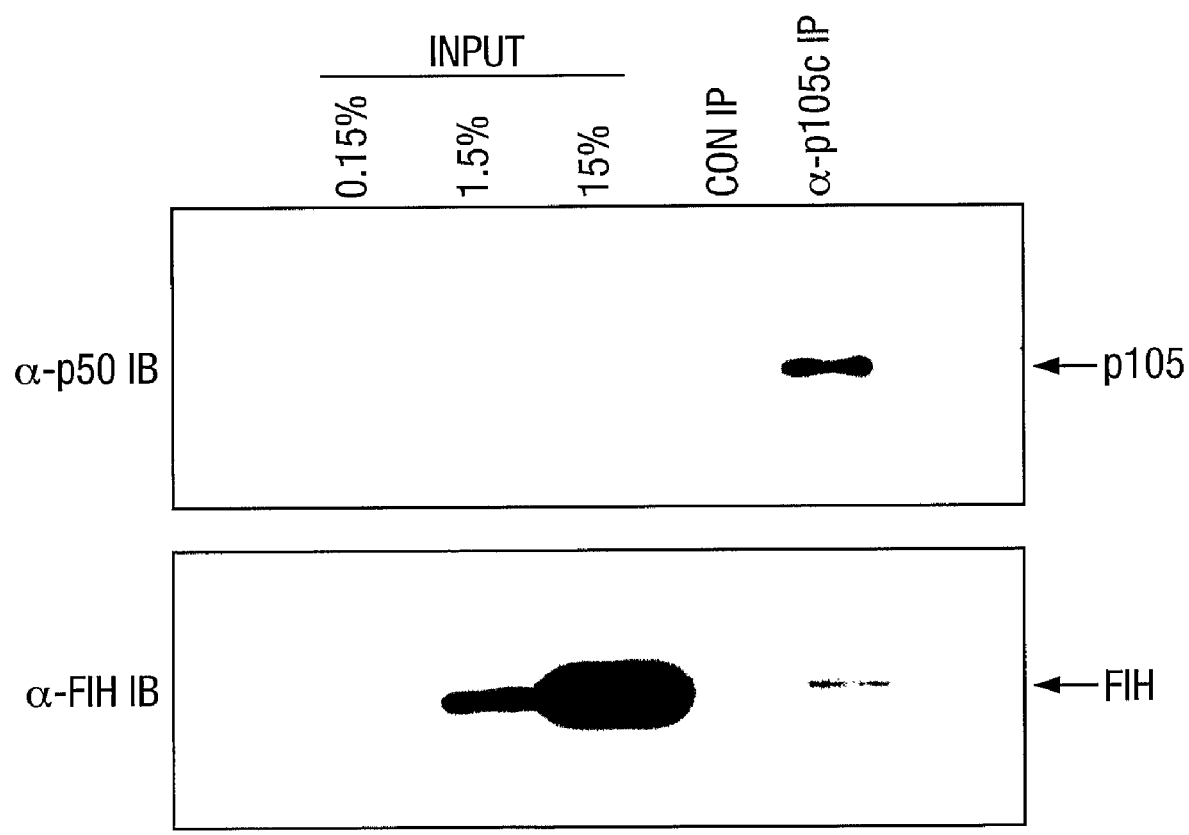
FIG. 2 shows the association of endogenous FIH and p105 protein in HeLa cells. A). Cell lysate (INPUT) together with anti-p 105 (α-p105c IP) and control (CON IP) immunoprecipitates were immunoblotted with anti-p105 antibody (α-p50 IB) to confirm retrieval of p105 protein, and anti-FIH antibody (α-FIH IB). The anti-FIH immunoblot indicates specific retrieval of FIH in the p105 immunoprecipitate.

To determine if an endogenous interaction exists between FIH and p105/IκBα in tissue culture cells, co-immunoprecipitation experiments were performed using extracts from HeLa and U2OS cells. Anti-p105 immunoprecipitations were performed and probed with anti-FIH antibody. FIH was detected in the p105, but not in control immunoprecipitates (FIG. 2). To analyse the IκBα/FIH interaction, FIH immunoprecipitations were performed and immunoblotted with anti-IκBα antibody. IκBα was specifically detected in the FIH, but not the control immunoprecipitates. These data indicate that endogenous FIH can associate with the ankyrin repeat domain-containing proteins (p105 and IκBα) in cultured cells.

EXAMPLE 4

FIH can Hydroxylate Proteins other than HIF-α

Highly purified (>95% pure) recombinant FIH was incubated individually with each of the p105, IkappaB-alpha and FEM-1 peptides as potential substrates using an assay that measures decarboxylation of 2OG. The results clearly indicate that decarboxylation of 2OG is stimulated in the presence of these alternative substrates in an amount roughly equivalent to HIF-1α CAD. Both the GST-fused and the free form of a polypeptide encompassing the ankyrin repeat domain (ARD) of p105 also caused significant stimulation of FIH mediated 2OG turnover. Mutation of the proposed asparaginyl residue to be hydroxylated by FIH in p105 ARD to an alanine residue led to a substantial decrease in 2OG turnover. Incubation of FIH with IkappaB-alpha under standard assay conditions also stimulated turnover to a similar extent as observed for p105 ARD (Table 2).

TABLE 2

| Substrate | % activity relative to GST HIF-1α 786-826 |
|---|---|
| GST HIF-1α 786-826 | 100 |
| HIF-1α 788-806 (19 mer) | 75 |
| p105 21 mer | 100 |
| IkBa 21 mer | 111 |
| FEM-1 21 mer | 89 |
| p105 ARD | 164 |
| GST p105 ARD | 129 |
| GST p105 ARD N to A mutant | 12 |
| IkappaB-alpha | 144 |

Figure 3:
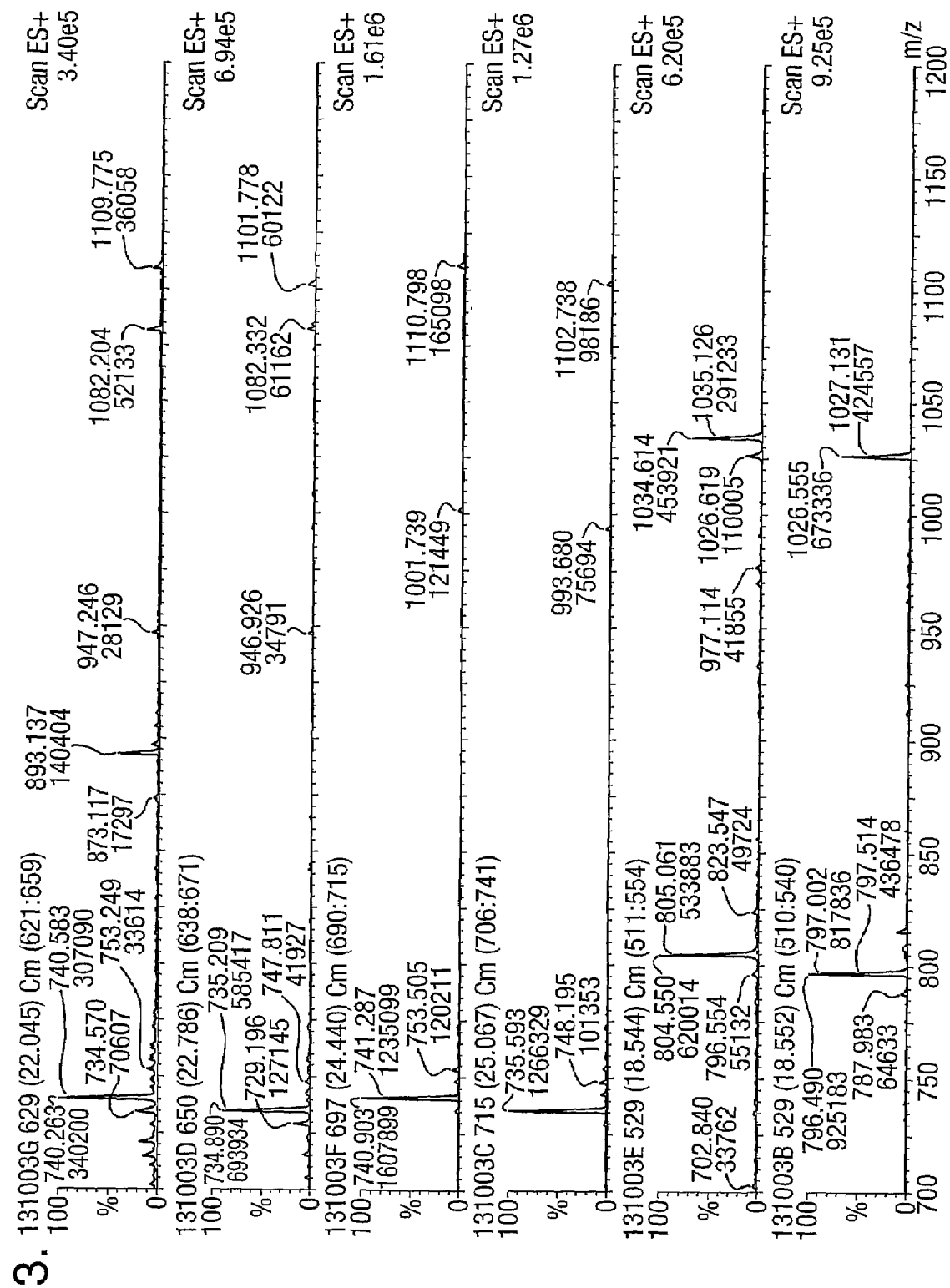
FIG. 3 illustrates the LC-MS analysis of FIH treated peptide. From top to bottom: (1) FEM-1+FIH, (2) FEM-1 only, (3) IkappaB-alpha+FIH, (4) IkappaB-alpha only, (5) CAD+FIH, (6) CAD only.

To check for direct peptide substrate hydroxylation, assay mixtures with each of the peptide substrates were analysed by both NMR and LC-MS. Using the latter technique both the FEM-1 and IkappaB-alpha peptides were observed to be hydroxylated under standard assay conditions (FIG. 3). 2D-NMR spectra of the both the p105 and FEM-1 peptide after incubation with FIH under standard assay conditions were consistent with asparaginyl hydroxylation, as seen previously for synthetic HIF-1α 788-806.

EXAMPLE 5

Additional Ankyrin Peptide Substrates for FIH

It was found that additional ankyrin peptide substrates for FIH include the following:

p19-INK-4-d—Cyclin-dependent kinase 4/6 (CDK) inhibitor

GABPbeta [GA binding protein]—Transcriptional regulator that binds GABPalpha

Tankyrase ½—Poly (ADP-ribose) polymerase, binds multiple substrates including TRF1, IRAP and Grb14

2-5A-d-R [2-5A(adenine)-dependent RNase (RNase L)]—Endoribonuclease

Gankyrin—Regulator of Rb (retinoblastoma) protein, binds CDK4/cyclin D,Rb

Myotrophin—Developmental regulator, binds NFkappaB

M110 [MYPT1]—Regulator of myosin phosphorylation, binds protein phosphatase 1c

FGIF [Factor Inducing Foetal Globin]—Regulator of foetal Hb expression.

Descriptions of the biological activities (or references to relevant papers) of the corresponding ankyrin proteins are given in "The ankyrin repeat as molecular architecture for protein recognition" Mosavi, L K et al. (2004) Protein Science 13:1435-1448.

TABLE 3

| Substrate | Activity + FIH (relative to synthetic HIF1alphaCAD)* | Hydroxylation of peptide observed by LC-MS analysis** |
|---|---|---|
| CAD | 100 | Yes |
| p19-INK-4d | 124 | Yes |
| GABPbeta | 107 | Yes |
| Tankyrase 1/2 | 107 | Yes |
| 2-5A-d-R | 27.8 | Yes |
| Gankyrin/p28-II | 116 | Yes |
| Myotrophin | 154 | Yes |
| M110 | 122 | Yes |
| FGIF | 168 | Yes |

*CAD is a HIF C-terminal transactivation domain standard peptide whose sequence is shown in Table 1 above.
**LC-MS analyses located the site of hydroxylation to the internal asparagine residue in the case of tankyrase.

EXAMPLE 6

Tryptic Direst and Mass Spectrometric Analyses of p105

Tryptic digest analysis was used for verification of the site of hydroxylation in p105 and IkappaB-alpha. Consideration of the p105 tryptic digest pattern revealed, however, that the tryptic peptide produced from p105, proposed to contain the modified asparaginyl residue, could be too large both for analysis in MALDI reflectron mode and for sequencing to the Asn residue using either CAF or MS/MS techniques. Consequently a p105 ARD L668K mutant was made that produced a tryptic fragment of mass 1,526 Da. This mutant was expressed as for the wild-type p105 ARD and purified using the same protocols. Following incubation with FIH under standard assay conditions, the p105 and FIH were separated by SDS-PAGE (12.5% gel). After excision of the p105 from the gel, a tryptic digest was performed both on the assay sample and on a p105 sample that had not been incubated with FIH. The resulting samples were analysed by MALDI ToF mass spectrometry.

The results clearly show that following incubation with FIH, a peak at 1,542 Da appears in the spectrum that corresponds to the hydroxylated 1,526 Da peptide i.e. +16 Da. This peak is absent from all p105 samples so far analysed without an FIH incubation or with other controls.

Recombinant IκB-α was incubated with FIH under standard assay conditions followed by tryptic digestion. The resulting tryptic fragments were analysed using both linear and reflectron mode MALDI-TOF mass spectrometry. The results demonstrated hydroxylation of the fragment.

EXAMPLE 7

Hydroxylation of p105 Using an Endogenous Source of FIH

Figure 4:
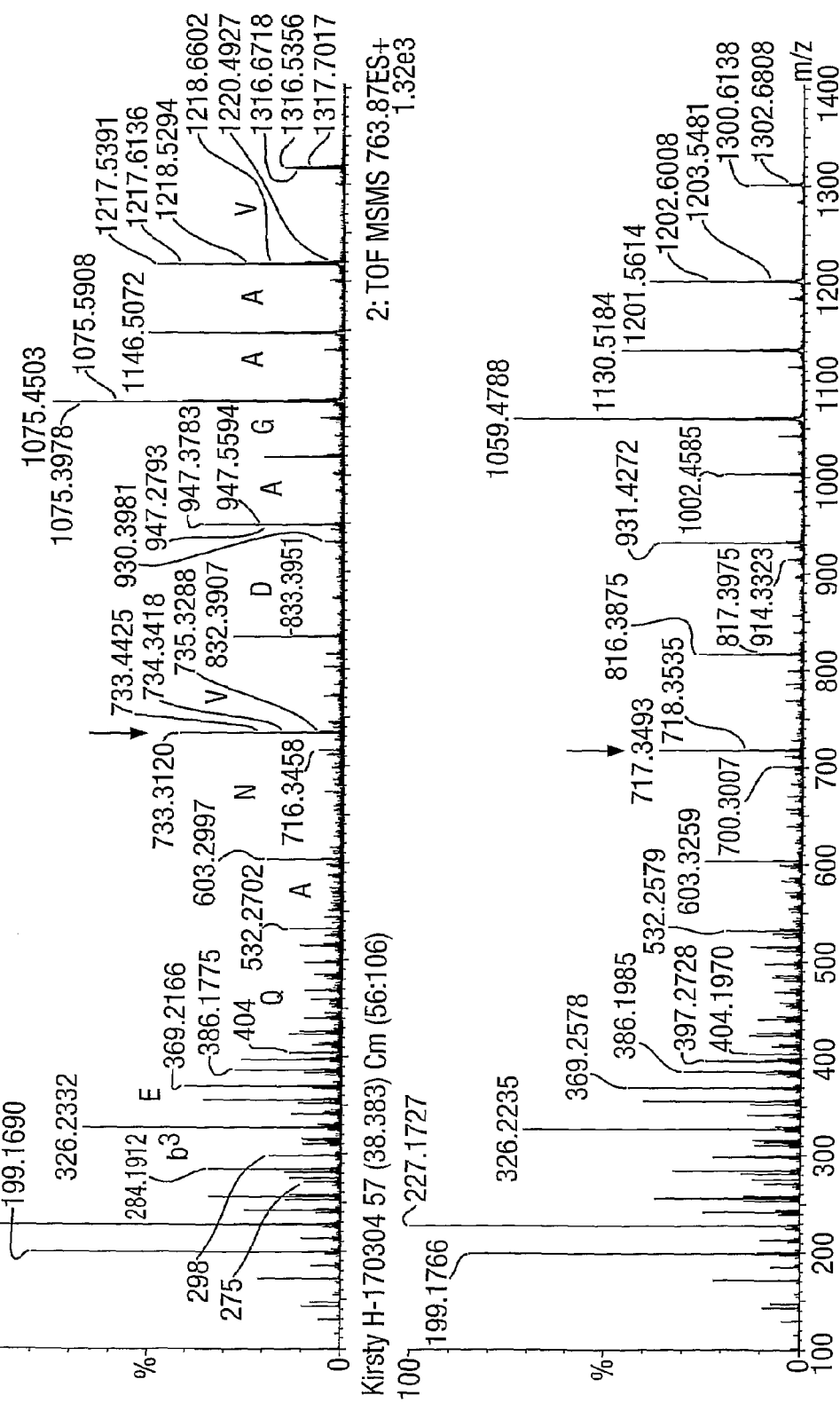
FIG. 4 shows the results of electrospray ionization MS/MS analysis of a tryptic digest fragment from p105 containing the hydroxylated asparaginyl residue.

To demonstrate in vivo hydroxylation of p105, cells were transfected with a full length p105 L668K/R870A mutant. A second mutation was introduced to remove the production of a peptide of mass 1,542 Da (not present in p105 ARD) that would overlap with the expected hydroxylated peptide. Tryptic digestion or protein recovered from gel purification of p105 L668K/R870A was carried out and the sample analysed by LC-MS using electrospary ionization MS/MS. MS/MS analyses identified the correct sequence of the expected peptide (VAAGADVNAQE, SEQ ID NO:4), and demonstrated the position of hydroxylation to be Asn778 (FIG. 4).

X-ray crystal structures are available for the following biological ANK proteins in addition to two designed consensus-sequence artificial ANK proteins (PDB-ID in brackets); Ankyrin-R (1n11), 53BP2-p53 (1ycs), GA-binding protein (1awc), cell cycle inhibitors p19ink4D (1bd8, 1bi8, 1b1x), p18Ink4C (1ihb, 1 g3n, 1bu9), p16ink4A (1bi7), IκB-α-(p50-p65 heterodimer complex) (1ikn, 1nfi), IκB-β (1oy3, 1k3z), Bcl3 (1k1a, 1k1b), Notch NICD (1ot8), Swi6 (1sw6), Pyk-2 associated protein β (1dcq), Sank E3_5 artificial ANK protein (1mj0), 3ANK artificial ANK (1n0q) and the 4ANK artificial ANK (1n0r).

The consensus-sequence (Main et al. Curr Opin Struct Biol (2003) 13 482-489) for the ANK-repeat contains the conserved motif DVNA, of which the asparaginyl residue can be hydroxylated as described above. The DVNA motif is part of a "bulge" before the beta-hairpin turn linking the repeats.

Figure 5:
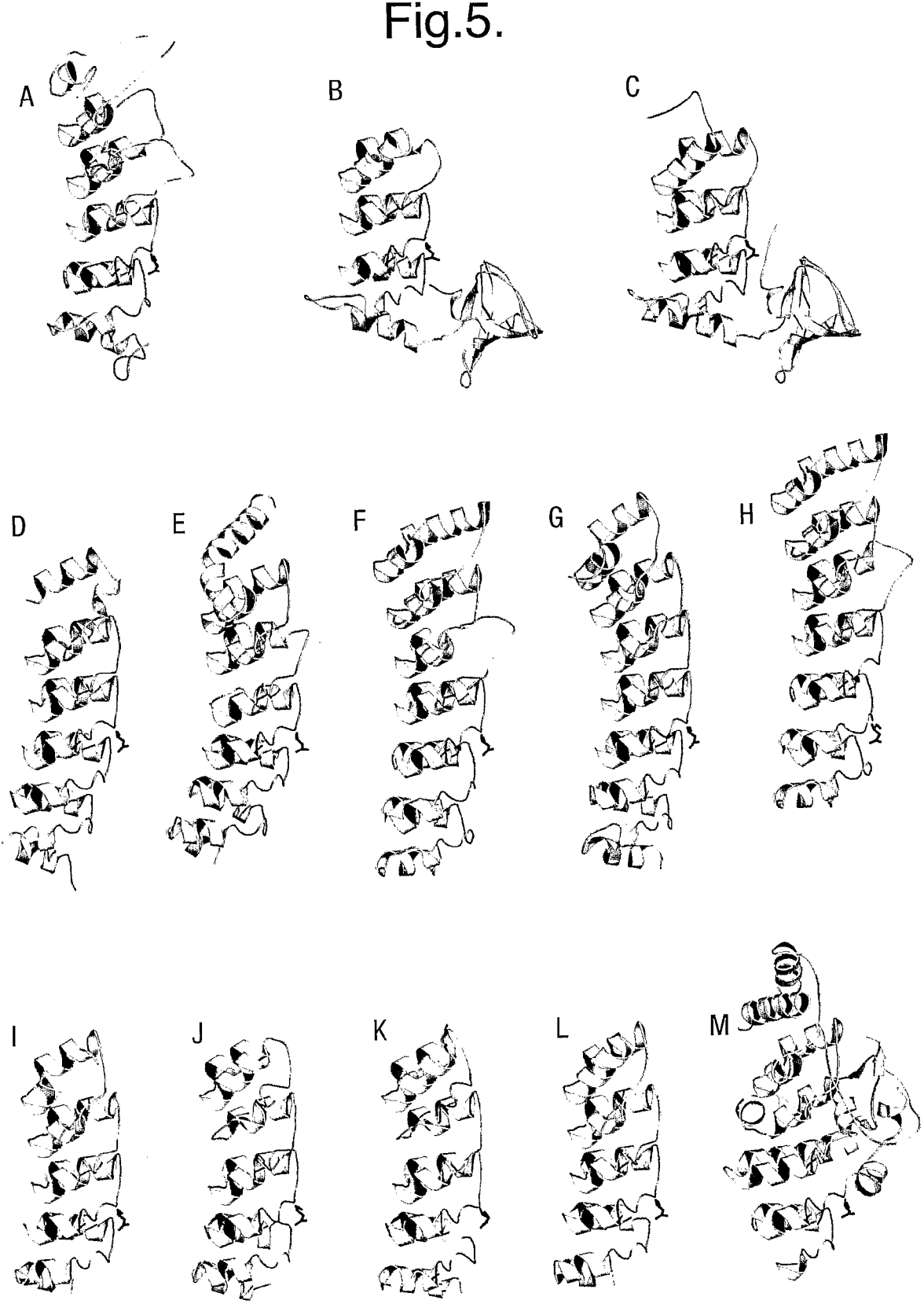
FIG. 5 is a ribbons representations of 13 ANK-proteins showing the asparagine black sticks A IkB-α; B 53BP2; C iASPP; D FEM1-b; E Notch; NICD; F p105 (NFkB-1); GUACA; H bcl-3; I ILK; J p18INK4C; K p19INK4D; L GABP-b; M swi6.

Superposition of the ANK crystal structures and modeled structures based on the Y2H results show that, in the structures analysed the DVNA motif occurs between the same register repeats ($4^{th}$ and $5^{th}$) of the ANK proteins (FIG. 5). Each of the crystal structures was obtained using bacterially expressed recombinant protein and provides an explanation as to why hydroxylation at the corresponding asparagine was not observed since there are no FIH-1 homologs and very few uncharacterized JmjC domain proteins in the bacterial genome.

Figure 6:
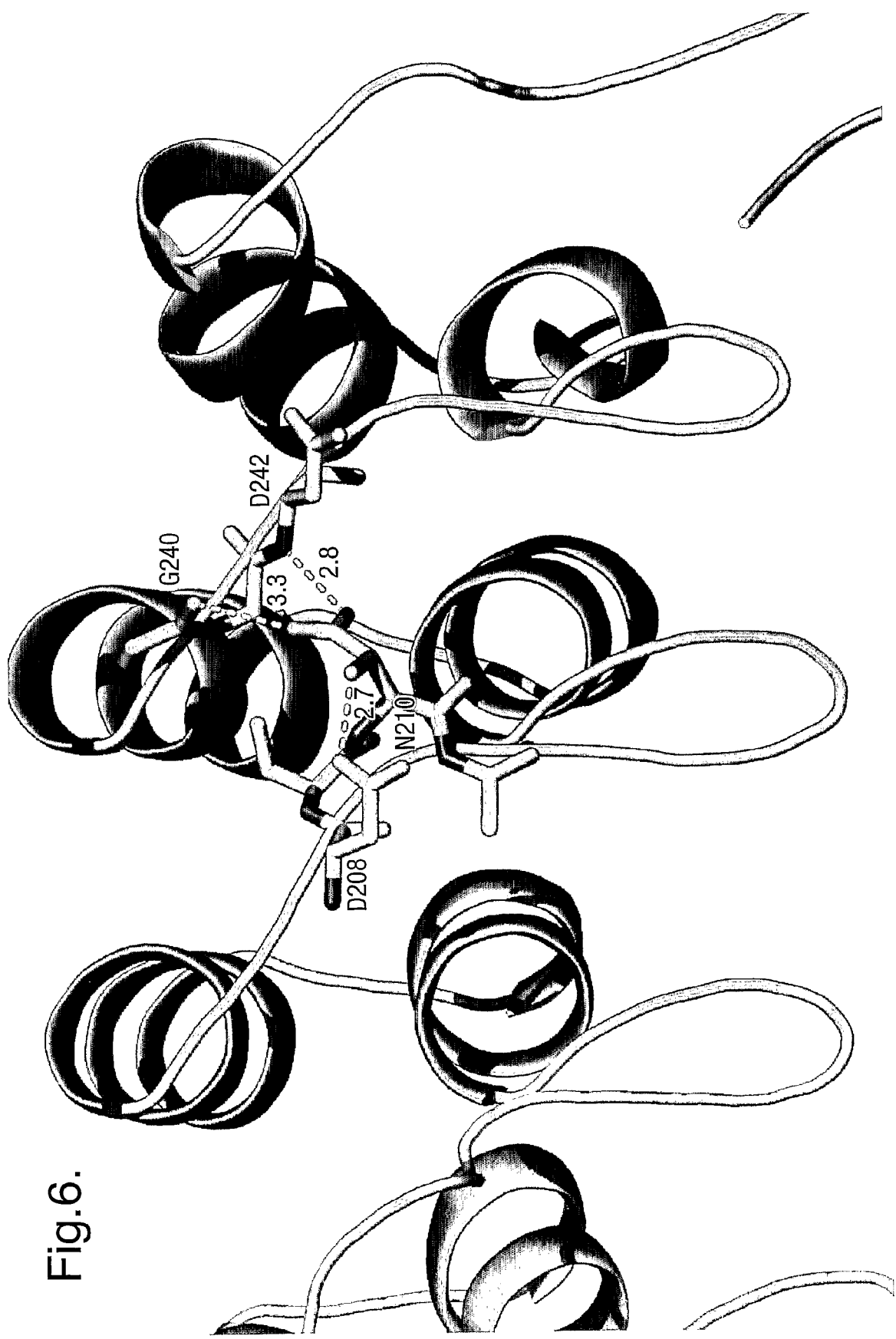
FIG. 6 is a ribbons representation of IκB-α (1ikn). DVNA (208-211) motif (note the beta-bulge) displayed as stick with H-bonds (dashed lines) from Asn210 (N210) side-chain to the backbone atoms of repeat 5. Modeling a hydroxyl group on Asn210 Cβ, in the same stereochemistry (pro-S) as is found for hydroxylated HIF-1α, shows how the creation of a H-bond between the side chain of Asp208 (D208) and the introduced hydroxyl of Asn210 may stabilize the beta-bulge. Residues Gly240 (G240) and Asp242 (D242) are also shown. The numbers 2.7, 2.8, and 3.3 are the lengths of the hydrogen bonds in Angstroms.
Figure 7:
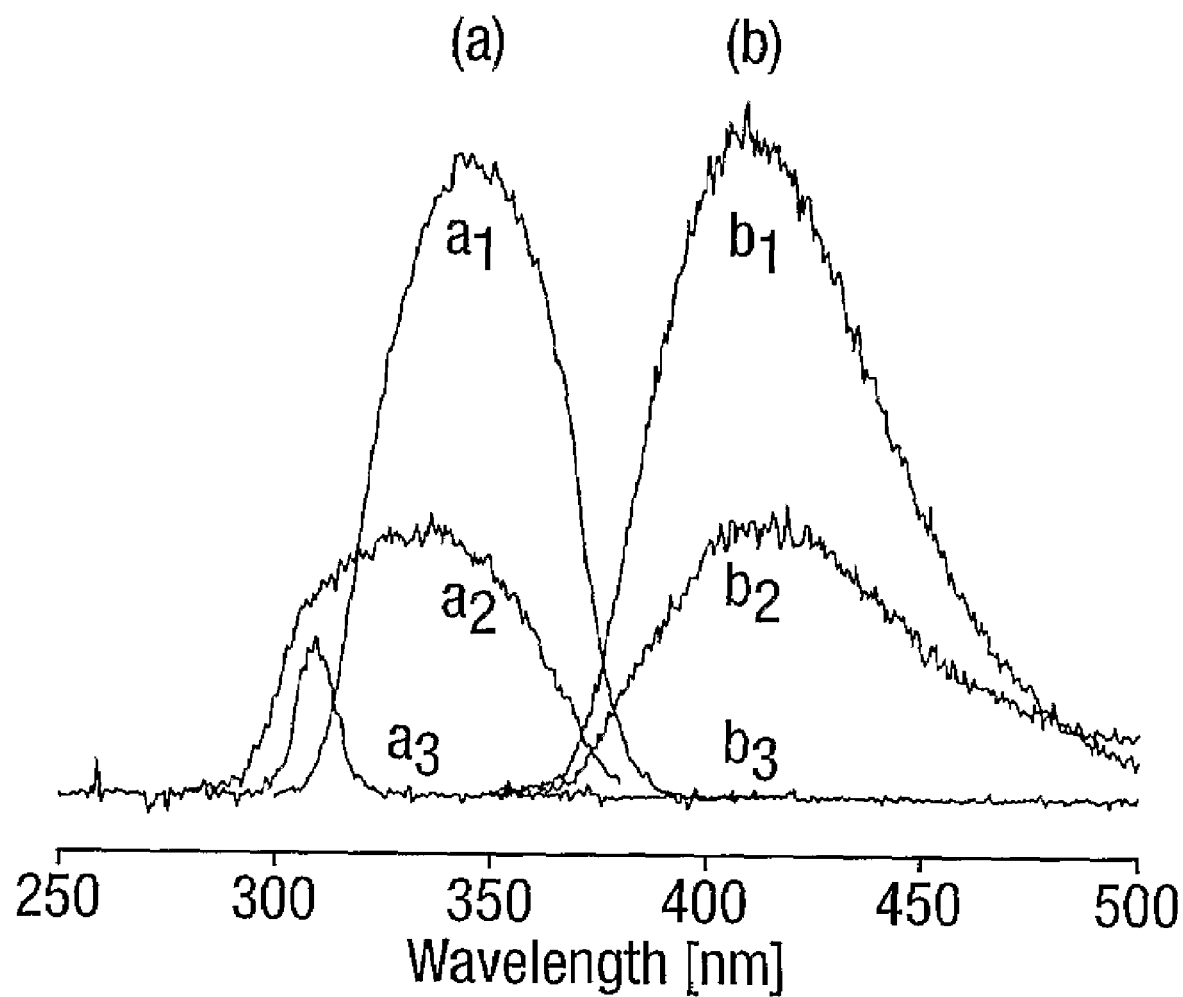
FIG. 7 shows the results of mass spectrometric analyses that characterise the product of the reaction between OPD and 2-oxoglutarate. a) Excitation (emission=420 nm) and b) emission (excitiation=340 nm) spectra of: 1) 125 μM Quinoxalinone in 0.25 M NaOH solution, 2) 250 μM in 0.5 M HCl solution 3) 10 mg/ml OPD in 0.5 M HCl.

The DVNA motif of IκB-α occurs as a bulge on the loop between its $4^{th}$ and $5^{th}$ ANK repeats. Asn210 atoms OD1 and ND2, of repeat 4 position 29, make H-bond interactions with loop backbone atoms Gly240 O (3.3 Å) and D242 N (2.8 Å) atoms, of repeat 5 position 25 and 27, respectively (FIG. 6). For this reason, the asparaginyl residue is not particularly exposed to solvent. Modeling the interaction between FIH and IκB-α suggests that a conformational change of the IκB-α repeat 4 loop is required for hydroxylation by FIH to occur. Modeling hydroxylation of the IκB-α asparaginyl residue at the pro-S position, as determined for HIF-1α, creates a H-bond between Asp208 (repeat 4, position 27) and the introduced hydroxyl group on Asn210 at repeat position 29 (FIG. 6). The presence of an additional H-bond may increase the stability of the protein or provide a new site for protein-protein recognition/stability.

It has been reported that pirin, a JmjC domain protein, interacts with Bcl-3, an ANK-protein (Dechend et al. Oncogene (1999) 18 3316-3323). The modeled interaction between the crystal structures of pirin and bcl-3 shows that the DVNA motif of Bcl-3, which is between the $5^{th}$ and $6^{th}$ repeats in bcl-3, is situated in the active site of pirin (Pang et al. J. Biol. Chem. (2004) 279 1491-1498). Though no catalytic activity has been shown for pirin, its metal is coordinated by three histidines and an aspartic acid and it contains a double beta-helix motif similar to that of quercitin 2,3 dioxygenase. Its interaction with the ANK-protein Bcl3, which is structurally related to the ANK-protein IκB-α, suggests an evolutionary relationship between these two different JmjC-ANK interactions.

EXAMPLE 8

High Throughput Assay for Determining Hydroxylation by 2-oxoglutarate Dependent Oxygenases OPD was bought from Across Organics and recrystallised from heptane and petroleum ether (120-140). DTT was from Melford Laboratories. Catalase and iron ammonium sulphate were from Sigma. FIH and GST-tagged HIF 786-826 were prepared as described previously(Hewitson, et al. J. Biol. Chem. 2002 26351-26355).

Scanning emission and excitation spectra were recorded on a Perkin Elmer LK-50B spectrometer.

The assay of FIH activity was carried out by mixing 1 mM DTT, 0.6 mg/ml catalase, 2OG, substrate and 50 mM Tris/HCl pH 7.5 to a final volume of 88 microl and warming to 37° C. for 5 minutes in a water bath. Simultaneously, the enzyme and iron (prepared as 500 mM stock in 20 mM HCl, and diluted with water) were mixed at room temperature for 3 minutes. Reaction was initiated by addition of 12 microl of enzyme/iron mix to the substrate/cofactor mix. The reaction was stopped by addition of 200 microl 0.5M HCl; derivatisation was then achieved by the addition of 100 microl 10 mg/ml OPD in 0.5M HCl, and heating for 10 minutes at 95° C. in a heating block. After centrifugation at top speed in a bench microfuge for 5 minutes, the supernatant (50 microl) was made basic by the addition of 30 microl 1.25M NaOH and the fluorescence was measured on a Novostar (BMG Labtechnologies Ltd.) with the excitation filter at 340 nm and the emission filter at 420 nm The product of the reaction between OPD and 2-oxoglutarate was characterised by $^1H$ and $^{13}C$ nmr and by mass spectrometry, confirming that the cyclisation reaction proceeded as expected to give the fluorescent product.

NMR data:

$^1$H-NMR (DMSO-D$_6$) δ [ppm]: 7.71 (m, 1H, CH$_{Ar}$), 7.50 (m, 1H, CH$_{Ar}$), 7.30 (m, 2H, CH$_{Ar}$), 3.03 (t, 2H, CH$_2$), 2.74 (t, 2H, CH$_2$)

$^{13}$C-NMR (DMSO-D$_6$) δ [ppm]: 174.7 (C$_{quart}$), 161.1 (C$_{quart}$), 155.4 (C$_{quart}$), 132.5 (C$_{quart/Ar}$), 132.3 (C$_{quart/Ar}$), 130.3 (CH$_{Ar}$), 128.9 (CH$_{Ar}$), 123.9 (CH$_{Ar}$), 116.1 (CH$_{Ar}$), 30.4 (CH$_2$), 28.5 (CH$_2$).

Fluorescence spectra of 1 revealed that the maximum response was obtained under basic conditions, exciting at 340 nm and measuring the emission at 420 nM.

Figure 8:
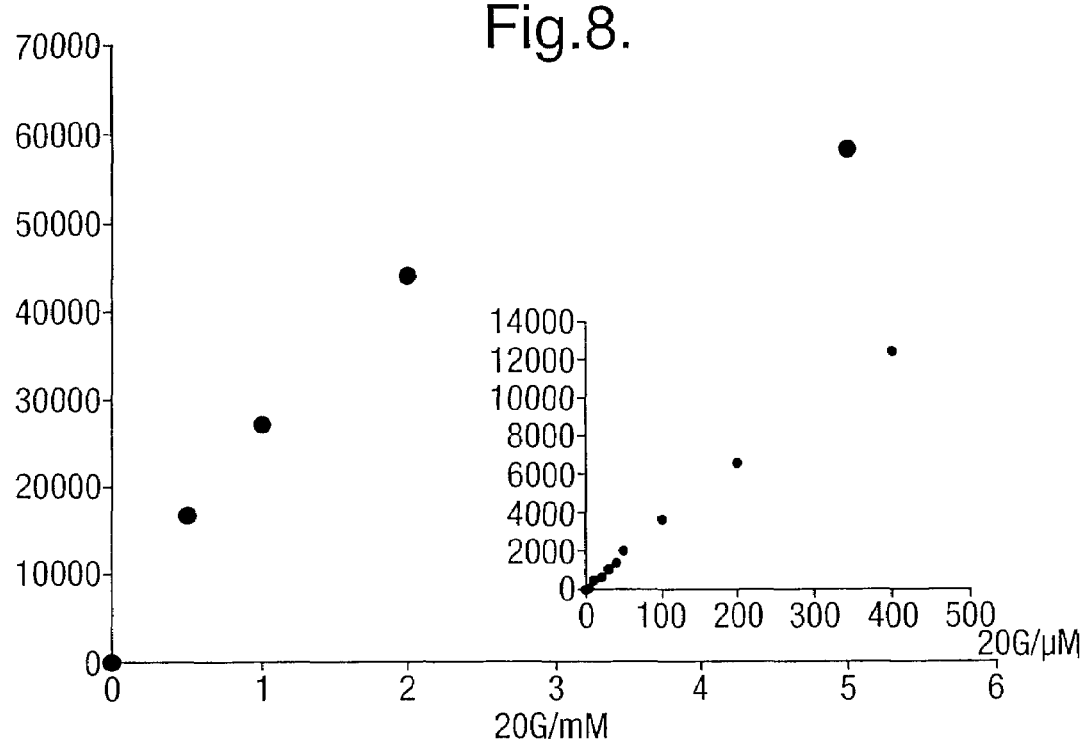
FIG. 8 illustrates the reaction of OPD with varying concentrations of 2-OG. Concentrations quoted are concentration in 100 micol volume, made as described in the assay section.
Figure 9:
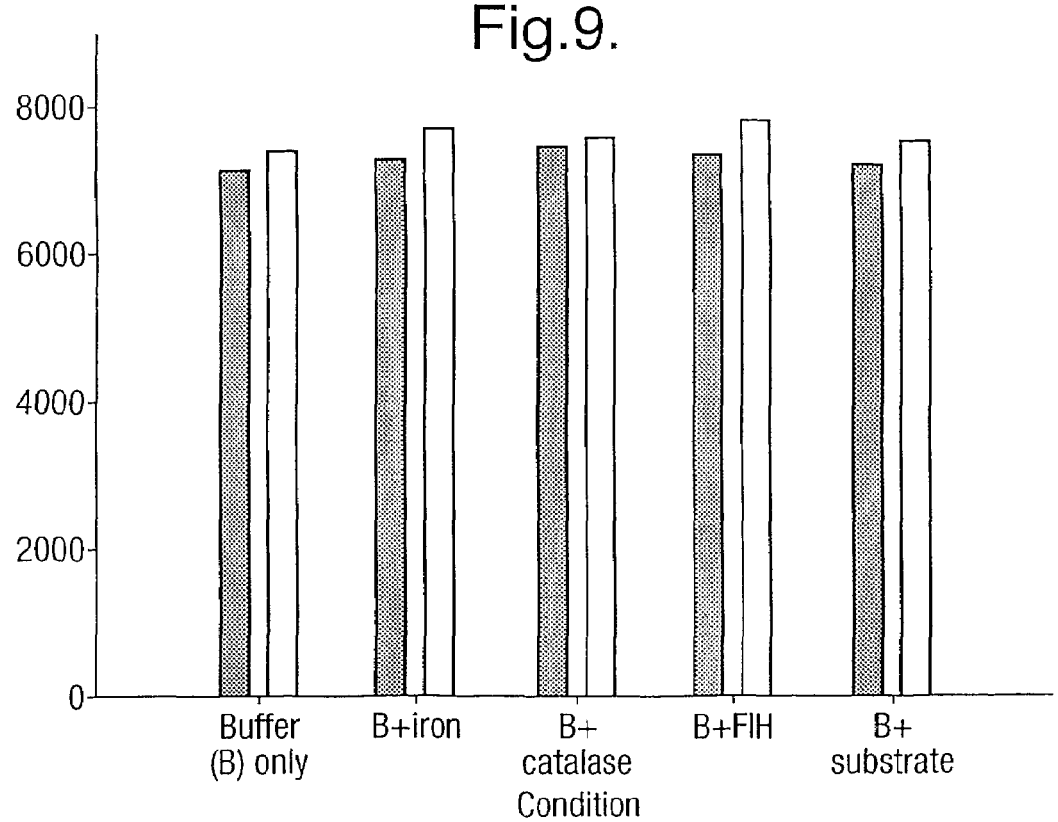
FIG. 9 is a chart showing the effect of the assay components on the fluorescence generated during an incubation. Black bars=no incubation, grey bars=15 minute incubation. Buffer=50 mM Tris/HCl pH 7.5.

Linearity of the developed fluorescence with respect to the concentration of 2OG was demonstrated up to 1 mM 2OG (FIG. 8), and it was shown that the presence of GST, FIH, catalase, DTT, and Fe, both separately and in combination had no appreciable effect on the development of fluorescence up to the highest concentrations used in the assay procedure reported here (FIG. 9).

EXAMPLE 9

Demonstration of Endogenous Hydroxylation of IκB-α

(a) Purification

A 5 liter suspension of HeLa S3 cells grown in DMEM was pelleted by centrifugation and resuspended in 250 ml of Igepal 16-30 lysis buffer (Sigma). The cell lysate was cleared by centrifugation at 20,000 g for 20 minutes. 25 ml of protein A-SEPHAROSE™ bead conjugates were first added to the cell lysate and incubated overnight at 4° C. to precipitate proteins that non-specifically interacted with the SEPHAROSE™ beads. IκB-α 10B antibodies were conjugated to SEPHAROSE™ beads and incubated with the cell lysate for 8 hours with rotation at 4° C. The supernatant was removed and retained for analysis by SDS-PAGE/Western blot. The antibody-SEPHAROSE™ bead conjugates were washed 7 times with 50 volumes of lysis buffer, to remove proteins non-specifically associated with the conjugates. IκB-α was eluted from the antibodies using 4 ml 10 mM glycine, pH 2.5 and concentrated by precipitation with 10% trichioroacetic acid. The precipitate was washed with 100 μl of cold acetone, resuspended in 100 μl of 1X SDS-PAGE loading buffer and subjected to SDS-PAGE analysis.

(b) Trypsin Digestion

IκB-α was obtained via immunoprecipitation described in (a). Bands corresponding to IKBA were excised from the gel, cut into ~1 mm squares and washed extensively with water. The gel pieces were then washed with 100 μl 50% acetonitrile for 15 minutes with shaking. After removing the supernatant, the gel pieces were incubated in 50 μl acetonitrile at room temperature without shaking, for. After 5 minutes, excess acetonitrile was removed and the gel pieces were rehydrated in 50 μl 0.1 M ammonium bicarbonate (Sigma). After a further 5 minutes, 50 μl acetonitrile was added and the mixture incubated at room temperature without shaking. After 15 minutes, all excess liquid was removed and the gel pieces were dried in a SPEEDVAC™.

The dried gel pieces were rehydrated in 50 λl 10 mM DTT (dissolved in 0.1 M ammonium bicarbonate) and incubated at 56° C. for 45 minutes. Excess DTT was removed, 50 μl of 55 mM iodoacetarnide (dissolved in 0.1 M ammonium bicarbonate) added and incubated at room temperature for 30'. All excess liquid was removed and the gel pieces were washed again with ammonium bicarbonate/acetonitrile as described above. The gel pieces were dried in a SPEEDVAC™ and resuspended in 50 μl of 20 μl/ml porcine trypsin (Promega) and incubated overnight at 37° C.

After incubation, the supernatant was transferred to a clean tube and the gel pieces were washed with 100 μl 25 mM ammonium bicarbonate for 5 minutes, with shaking. An additional 100 μl acetonitrile was added and left shaking for a further 60 minutes. The supernatant was removed and retained. The gel pieces were washed with 100 μl 0.1% trifluoroacetic acid (Fischer) for 5 minutes, with shaking. An additional 100 μl acetonitrile was added and left shaking for a further 60 minutes. All supernatants were pooled and dried in a SPEEDVAC™. The pellet was resuspended in 20 μl 0.1% trifluoroacetic acid and incubated overnight at 50° C. All liquid was dried in a SPEEDVAC™ and resuspended in 5% acetonitrile/0.1% formic acid, prior to mass spectrometry.

(c) Mass Spectrometry

Liquid Chromatography/Mass spectrometry (LC/MS) was performed using a C4 Jupiter HPLC column (Phenomenex). Peptides were separated using a linear gradient of 5-95% acetonitrile/0.1% formic acid and analysed using a Waters Q-TOF™ MICROMASS™ Spectrometer. Hydroxylated IκB-α eluted from the column after 8.5 minutes and the identity of the peptide (CGADVN*R (SEQ ID NO:23, with N defined as follows) was confirmed by tandem mass spectrometry (MS/MS) where N* corresponds to the hydroxylated asparagine residue. (The N-terminal cysteine was modified by alkylation and susbequent dehydration).

The invention claimed is:

1. A method of identifying an agent which modulates 2-oxoglutarate dependent oxygenase activity, the method comprising: contacting a 2-oxoglutarate dependent oxygenase and a test agent in the presence of a substrate comprising one or more ankyrin repeat sequences, in conditions under which the substrate is hydroxylated in the absence of the test agent; and determining hydroxylation of the substrate_thereby determining whether or not the agent modulates 2-oxoglutarate dependent oxygenase activity.

2. A method according to claim 1, wherein the substract is hyroxylated at an asparagine residue.

3. A method according to claim 2, wherein the asparagine residue is part of a valine-asparagine, aspartate-valine-asparagine, isoleucine-asparagine or leucine-asparagine sequence.

4. A method according to claim 1, wherein the substrate is IκB-α, p105, FEM-1, p19-INK-4d, GABPbeta, Tankyrase ½, 2-5A(adenine)-dependent RNase (2- 5A-d-R), Gankyrin, Myotrophin, M110, FGIF (Factor Inducing Foetal Globin), or a fragment thereof comprising one or more ankyrin repeat sequences.

5. A method according to claim 4, wherein the substrate is p105 or a fragment thereof comprising Asn 778 of p105 or a peptide analogue of p105 or fragment thereof comprising an asparagine equivalent to Asn 778 of p105 and wherein hydroxylation of Asn 778 or of a said equivalent asparagine is determined.

6. A method according to claim 1, wherein the 2-oxoglutarate dependent oxygenase is a JmjC protein.

7. A method according to claim 6, wherein the JmjC protein is factor inhibiting hypoxia-inducible factor (FIH).

8. A method according to claim 1, wherein the hydroxylation of the substrate is determined by monitoring 2-oxoglutarate turnover.

9. A method according to claim 1, wherein the hydroxylation of the substrate is determined by mass spectrometry.

10. A method according to claim 1, wherein the hydroxylation of the substrate is determined by monitoring for transcription or expression of a reporter gene driven by a promoter regulated by an ankyrin repeat protein.

11. A method according to claim 1 further comprising formulating an agent identified as a modulator of 2-oxoglutarate dependent oxygenase activity with a pharmaceutically acceptable recipient.

12. A method of identifying an agent which selectively modulates activity of a first 2-oxoglutarate dependent oxygenase, the method comprising:
(a)(i) contacting a first 2-oxoglutarate dependent oxygenase and a test agent in the presence of a substrate comprising one or more ankyrin repeat sequences, in conditions under which the substrate is hydroxylated in the absence of the test agent; and
(ii) determining hydroxylation of the substrate;
(b)(i) contacting a second 2-oxoglutarate dependent oxygenase and a test agent in the presence of a substrate comprising one or more ankyrin repeat sequences, in conditions under which the substrate is hydroxylated in the absence of the test agent; and
(ii) determining hydroxylation of the substrate;
thereby determining whether or not the agent selectively modulates activity of the first 2-oxoglutarate dependent oxygenase.

13. A method according to claim 12, wherein the test agent inhibits activity of the first 2-oxoglutarate dependent oxygenase.

14. A method according to claim 12, wherein the first 2-oxoglutarate dependent oxygenase is factor inhibiting hypoxia-inducible factor (FIH).

15. A method according to claim 12, wherein the second 2-oxoglutarate dependent oxygenase is a prolyl hydroxylase domain (PHD).

16. A method according to claim 12, wherein the first 2-oxoglutarate dependent oxygenase is a PHD.

17. A method according to claim 16, wherein the second 2-oxoglutarate dependent oxygenase is FIH.

18. A method according to claim 12, wherein the substrate is hydroxylated at an asparagine residue.

19. A method of identifying an agent which selectively modulates 2-oxoglutarate dependent oxygenase activity on a first substrate, the method comprising:
(a)(i) contacting a 2-oxoglutarate dependent oxygenase and a test agent in the presence of a first substrate, in conditions under which the substrate is hydroxylated in the absence of the test agent; and
(ii) determining hydroxylation of the first substrate; and
(b)(i) contacting a 2-oxoglutarate dependent oxygenase and a test agent in the presence of a second substrate, in conditions under which the substrate is hydroxylated in the absence of the test agent; and
(ii) determining hydroxylation of the second substrate;
wherein at least one of said first and second substrates comprises one or more ankyrin repeat sequences;
thereby determining whether or not the agent selectively modulates 2-oxoglutarate dependent oxygenase activity on a first substrate.

20. A method according to claim 19, wherein the first and/or second substrate comprising one or more ankyrin repeat sequences is hydroxylated at an asparagine residue.

21. A method according to claim 19, wherein the first substrate is HIF and the second substrate comprises one or more ankyrin repeat sequences.

22. A method according to claim 19, wherein the second substrate is HIF and the first substrate comprises one or more ankyrin repeat sequences.

23. A method according to claim 19, wherein the first and second substrates are different and each comprises one or more ankyrin repeat sequences.

24. A method according to claim 19, wherein the 2-oxoglutarate oxygenase is a Jmjc protein.

25. A method according to claim 1, wherein the test agent is a polypeptide comprising an ankyrin repeat sequence or an analogue thereof.

26. A method according to claim 25, wherein the analogue is an ankyrin repeat sequence that lacks an asparagine residue capable of being hydroxylated by 2-oxoglutarate dependent oxygenase.

* * * * *

UNITED STATES PATENT AND TRADEMARK OFFICE
CERTIFICATE OF CORRECTION

PATENT NO. : 7,638,295 B2  Page 1 of 1
APPLICATION NO. : 10/594295
DATED : December 29, 2009
INVENTOR(S) : Schofield et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 322 days.

Signed and Sealed this

Ninth Day of November, 2010

David J. Kappos
*Director of the United States Patent and Trademark Office*